(12) United States Patent
Anderson et al.

(10) Patent No.: US 12,178,452 B2
(45) Date of Patent: Dec. 31, 2024

(54) SURGICAL ROTATIONAL TOOL DRIVER AND METHOD

(71) Applicant: DEPUY IRELAND UNLIMITED COMPANY, Ringaskiddy (IE)

(72) Inventors: James Anderson, Batley (GB); Ian Flatters, Pensitone (GB); David Horne, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 423 days.

(21) Appl. No.: 17/607,222

(22) PCT Filed: Apr. 14, 2020

(86) PCT No.: PCT/EP2020/060469
§ 371 (c)(1),
(2) Date: Oct. 28, 2021

(87) PCT Pub. No.: WO2020/224919
PCT Pub. Date: Nov. 12, 2020

(65) Prior Publication Data
US 2022/0218362 A1 Jul. 14, 2022

(30) Foreign Application Priority Data
May 3, 2019 (GB) ..................... 1906313

(51) Int. Cl.
*A61B 17/16* (2006.01)
*A61B 17/00* (2006.01)

(52) U.S. Cl.
CPC ................ *A61B 17/1666* (2013.01); *A61B 2017/00473* (2013.01)

(58) Field of Classification Search
CPC ............ A61B 17/1666; A61B 17/1631; A61B 17/1617; A61B 17/1637; A61B 17/164
See application file for complete search history.

(56) References Cited

U.S. PATENT DOCUMENTS 5,658,290 A * 8/1997 Lechot ............... A61B 17/1666
606/80
5,980,170 A * 11/1999 Salyer ............... A61B 17/1677
408/239 R (Continued)

FOREIGN PATENT DOCUMENTS

| WO | 96/10962 A1 | 4/1996 |
| WO | 2018/033788 A1 | 2/2018 |
| WO | 2019/192793 A1 | 10/2019 |

OTHER PUBLICATIONS

PCT/EP2020/06049—International Search Report Mailed Jun. 23, 2020.
GB1906313.0—Search Report—Dated Oct. 31, 2019.

*Primary Examiner* — Amy R Sipp
(74) *Attorney, Agent, or Firm* — Barnes & Thornburg LLP

(57) ABSTRACT

A surgical rotational tool driver and method. The driver includes a driveline extending within a hollow shaft and a head part including connection features for connecting to a connection member of a surgical rotational tool. The connection features of the head part include a housing and a pair of jaw member each including jaws for receiving the connection member. Each jaw member is pivotally mounted for rotation between: a first position for receipt of the connection member and a second position for retaining the connection member. The connection features of the head part further include a locking mechanism including a pair of catches for engaging with a respective catch of each jaw member to lock the jaw members in the second position. The locking mechanism also includes a release member slideably moveable within the housing to release the catches of the locking mechanism from the catches of the jaw members.

18 Claims, 19 Drawing Sheets

(56) References Cited

U.S. PATENT DOCUMENTS

| | | |
|---|---|---|
| 9,078,672 B1 | 7/2015 | Rosse |
| 2009/0082771 A1* | 3/2009 | Weekes .................. B23B 31/18 408/124 |

\* cited by examiner

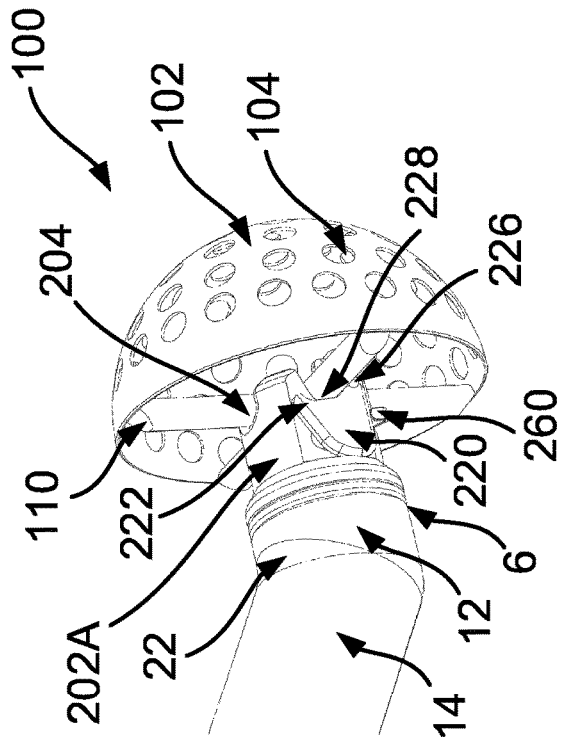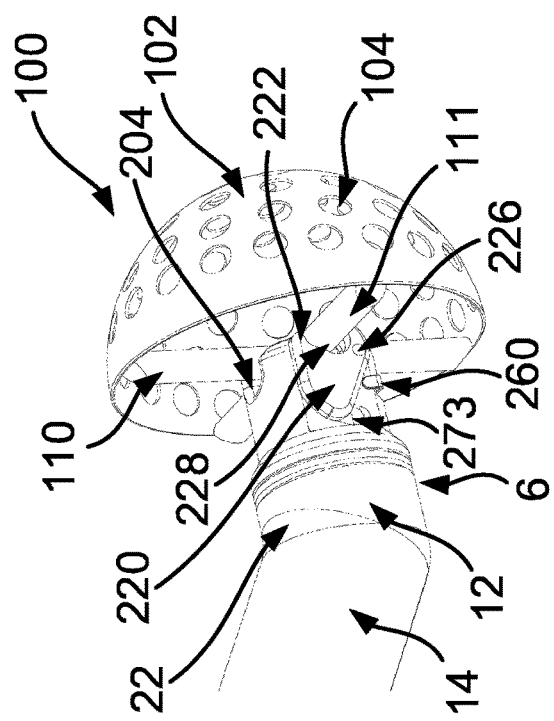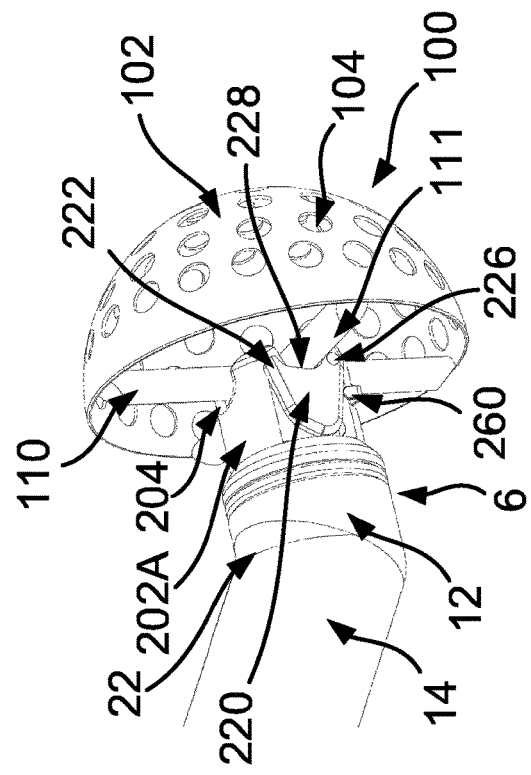
Fig. 14A
Fig 14B
Fig 14C

SURGICAL ROTATIONAL TOOL DRIVER AND METHOD

CROSS-REFERENCE TO RELATED APPLICATIONS

This application is a National Stage Application filed Under 35 U.S.C. § 371 of International Application No. PCT/EP2020/060469 filed Apr. 14, 2020, which claims priority to GB1906313.0 filed May 3, 2019, which are hereby incorporated by reference in their entireties.

FIELD OF THE INVENTION

This invention relates to a surgical rotational tool driver. This invention also relates to a method of operating a surgical rotational tool driver.

BACKGROUND OF THE INVENTION

Surgical rotational tool drivers allow torque to be transmitted to a surgical rotational tool from a rotational power tool. An example of a surgical rotational tool driver is an acetabular reamer driver for use with an acetabular reamer.

Hip replacement is a surgical procedure in which the hip joint is replaced by a prosthetic implant. As part of a hip replacement procedure, an acetabulum of the patient may be prepared for receiving an acetabular cup implant by reaming it to an appropriate size and depth. An acetabular reamer may have a substantially hemispherical dome to be received in the acetabulum. The acetabular reamer may also include features located on an outer surface of the dome for grating the inner surface of the acetabulum as the reamer rotates. The acetabular reamer may be releasably attached to a distal end of an acetabular reamer driver, to allow the surgeon to manipulate it (e.g. to position the dome within the acetabulum and to apply a force for pressing the reamer against the inner surface of the acetabulum as the reamer rotates). A driveline may extend within the acetabular reamer driver for transmitting torque to the acetabular reamer.

The acetabular reamer driver may include a release mechanism for releasing the acetabular reamer from the acetabular reamer driver.

SUMMARY OF THE INVENTION

Aspects of the invention are set out in the accompanying independent and dependent claims. Combinations of features from the dependent claims may be combined with features of the independent claims as appropriate and not merely as explicitly set out in the claims.

According to an aspect of the invention, there is provided a surgical rotational tool driver comprising:
  a substantially hollow shaft having a proximal end, a distal end;
  a driveline extending within the hollow shaft, the driveline having:
    a proximal end connectable to a rotational power tool for applying torque through the driveline; and
    a head part extending distally from the distal end of the shaft, the head part including connection features for connecting to a connection member of a surgical rotational tool, the head part having an axis of rotation for rotation of the surgical rotational tool on rotation of the driveline, the connection features of the head part comprising:
      a housing;
      a pair of jaw members, each jaw member including a pair of jaws for receiving the connection member of the surgical rotational tool, wherein each jaw member is pivotally mounted on the housing for rotation about an axis substantially perpendicular to the axis of rotation of the head part between:
        a first position for receipt of the connection member within the jaws of each jaw member; and
        a second position for retaining the connection member within the jaws of each jaw member to prevent removal of the surgical rotation tool from the surgical rotational tool driver; and a locking mechanism comprising:
        a pair of catches for engaging with a respective catch of each jaw member to lock the jaw members in the second position, and
        a release member slideably moveable within the housing to release the catches of the locking mechanism from the respective catches of the jaw members to allow the jaw members to return to the first position for removal of the surgical rotational tool from the surgical rotational tool driver.

According to another aspect of the invention, there is provided a method of operating a surgical rotational tool driver, the method comprising:
  connecting one or more connection features of a head part of a driveline of a surgical rotational tool driver to a connection member of a surgical rotational tool, the surgical rotational tool driver comprising:
    a substantially hollow shaft having a proximal end, a distal end;
    a driveline extending within the hollow shaft, the driveline having:
      a proximal end connectable to a rotational power tool for applying torque through the driveline; and
      said head part extending distally from the distal end of the shaft, the head part having an axis of rotation for rotation of the surgical rotational tool on rotation of the driveline, the connection features of the head part comprising:
      a housing;
      a pair of jaw members, each jaw member including a pair of jaws for receiving the connection member of the surgical rotational tool, wherein each jaw member is pivotally mounted on the housing for rotation about an axis substantially perpendicular to the axis of rotation of the head part between:
        a first position for receipt of the connection member within the jaws of each jaw member; and
        a second position for retaining the connection member within the jaws of each jaw member to prevent removal of the surgical rotation tool from the surgical rotational tool driver; and
      a locking mechanism comprising:
        a pair of catches for engaging with a respective catch of each jaw member to lock the jaw members in the second position, and
        a release member slideably moveable within the housing to release the catches of the locking mechanism from the respective catches of the jaw members to allow the jaw members to return to the first position for removal of the surgical rotational tool from the surgical rotational tool driver;

operating the release mechanism by sliding the release member within the housing; and removing the surgical rotational tool from the surgical rotational tool driver.

The jaw members of the claimed invention can provide for convenient mounting of a surgical rotational tool on the surgical rotational tool driver. Moreover, the locking mechanism including the catches and slideable release member can provide for a secure yet easily releasable connection between the surgical rotational tool driver and the surgical rotational tool.

The catches of the locking mechanism may each comprise a ramped surface extending laterally from the release member, and a retaining surface located at an end of the ramped surface. The catches of the jaw members are operable to ride along the ramped surface as the jaw members pivot from the first position to the second position and engage with the retaining surfaces when they reach the end of the ramped surface to lock the jaw members in the second position. This arrangement can allow the locking mechanism to be locked down by simple insertion of the connection member into the jaws of the jaw members. In particular, as the jaw members pivot and reach the second position, this automatically locks the jaw members because the catches of the jaw members engage with the retaining surfaces located at the ends of the ramps.

The release member may be slideably moveable within the housing to disengage the catches of the jaw members from the retaining surfaces of the catches on the release member. This can allow the jaw members to return to the first position, for convenient disconnection of the surgical rotational tool from the surgical rotational tool driver. In some embodiments, the release member may be slideably moveable along a direction substantially parallel to the axis of rotation of the head part.

The locking mechanism may further comprise a biasing element located within the housing for biasing the release member along the axis of rotation of the head part in a distal direction. This can bias the release member into a position in which the catches of the jaw members remain engaged with the retaining surfaces of the catches on the release member, whereby the secureness of the connection between the surgical rotational tool driver and the surgical rotational tool may be improved.

The housing may include an opening through which the catches of the jaw members engage with the ramped surface and the retaining surface of the catches on the release member. This can allow the jaw members to be located externally with respect to the housing, whereby their rotation during use does not interfere with the sliding movements of the release member, and vice versa.

The locking mechanism may further comprise a biasing element mounted on the housing further biasing the jaw members toward the first position. This can allow for the automatic return of the jaw members to the first position on operation of the release member.

The biasing element may comprise a leaf spring having a first end for biasing a first of the jaw members and a second end for biasing a second of the jaw members.

The release member may include at least one distally facing recess for receiving the connection member of the surgical rotational tool.

The driveline may be substantially hollow. The locking mechanism may further comprise an actuation member extending within the substantially hollow driveline. A distal end of the actuation member may be attached to the release member. The actuation member may be connected to the release mechanism for operating the release member from a position on the surgical rotational tool driver located proximally with respect to the head part. The provision of the actuation member within the driveline allows the release mechanism to be operated at a position that is located away from the distal end of the shaft. This may be more convenient for the surgeon, as the distal end of the shaft may not be easily accessible when it is located in the wound. Moreover, the provision of the actuation member within the driveline may allow an outer surface of at least the distal end of the shaft to be substantially free of clutter associated with the features (buttons, catches and the like) of a release mechanism, which may otherwise interfere with and damage soft tissue in the wound. In the absence of such features on its outer surface, the distal end of the shaft may thus have an uncluttered (e.g. smooth) and relatively narrow profile, which may also facilitate its easy insertion and extraction through the wound.

The substantially hollow shaft may have at least one bend and the driveline may have a universal joint located at each bend in the shaft.

The actuation member may be substantially flexible, to allow it to navigate any bends in the shaft. The actuation member may comprise a substantially flexible tension member, such as a wire.

The actuation member may be a polymer. The actuation member may comprise an alloy.

The or each universal joint may include a substantially hollow central portion through which the actuation member extends. This may allow the actuation member to extend within the driveline without interfering with the operation of the driveline. For instance, the or each universal joint may connect an end of a driveline section of the driveline to an end of another driveline section of the driveline. The or each universal joint may include a spider part pivotally attached to the end of each driveline section; and an aperture in the spider part. The actuation member may extend though the aperture.

The surgical rotational tool driver may be a reamer driver. For instance, the reamer driver may be an acetabular reamer driver. The surgical rotational tool may be an acetabular reamer.

According to another aspect of the invention, there is provided a surgical kit comprising a surgical rotational tool driver as defined in any of claims 1 to 16 and a surgical rotational tool having said connection member.

BRIEF DESCRIPTION OF THE DRAWINGS

Embodiments of the present invention will be described hereinafter, by way of example only, with reference to the accompanying drawings in which like reference signs relate to like elements and in which:

FIGS. 14A to 14C illustrate the attachment of a surgical rotational tool (such as an acetabular reamer) to the surgical rotational tool driver of FIG. 13.

DETAILED DESCRIPTION

Embodiments of the present invention are described in the following with reference to the accompanying drawings.

Figure 1:
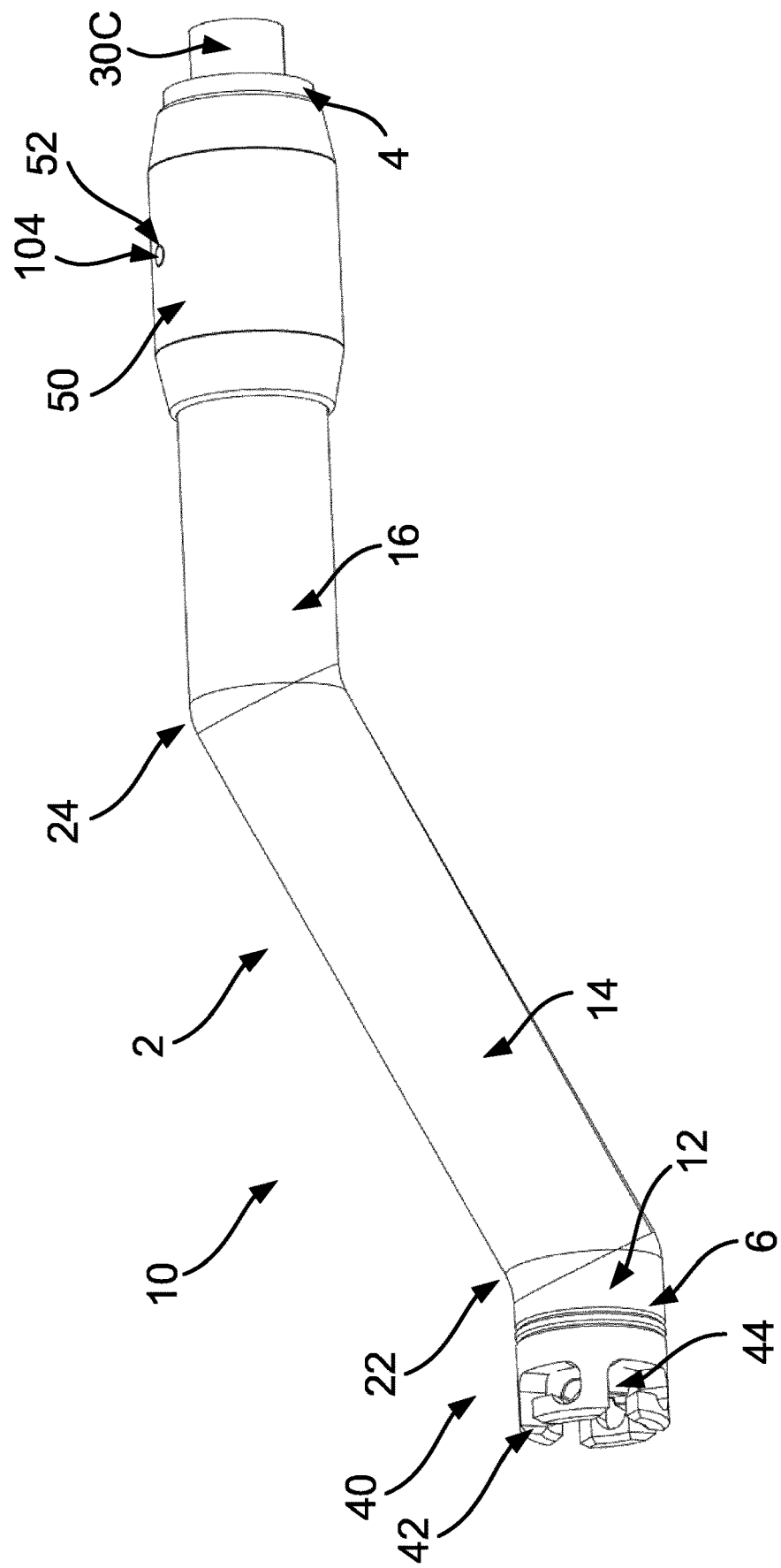
FIG. 1 shows a surgical rotational tool driver.

FIG. 1 shows a surgical rotational tool driver 10. The surgical rotational tool driver includes a substantially hollow shaft 2. The substantially hollow shaft 2 may be elongate. The substantially hollow shaft 6 has a proximal end 4 and a distal end 6.

The substantially hollow shaft 2 includes at least one bend. Each bend is located along the substantially hollow shaft 2, intermediate the proximal end 4 and the distal end 6. The surgical rotational tool driver 10 in this example is an offset driver including two bends 22, 24. It is envisaged however that the substantially hollow shaft 2 may include a single bend, or more than two bends.

In the present example, the bend 22 is located distally with respect to the bend 24. Each bend may be located at the interface between two shaft sections of the substantially hollow shaft 2. For instance, in the present example, the substantially hollow shaft 2 includes a distal shaft section 12, an intermediate shaft section 14 and a proximal shaft section 16. The distal shaft section 12 extends distally from the bend 22. The intermediate shaft section 14 extends between the bend 22 and the bend 24. The proximal shaft section 16 extends proximally from the bend 24. Each shaft section may be substantially cylindrical.

Each shaft section may have a longitudinal axis. The bend(s) may set the longitudinal axes of the various shaft sections at certain angles (e.g. ±30°, ±45°) to each other. The bend(s) in the substantially hollow shaft 2 may allow the surgeon to work around soft tissue in the wound space, while using the surgical rotational tool driver 10.

As shown in, for example, FIGS. 2A and 3 to 5, the surgical rotational tool driver 10 also includes a driveline 30. The driveline 30 is substantially hollow. The driveline 30 extends within the substantially hollow shaft 2. The driveline 30 allows torque to be transmitted through the surgical rotational tool driver 10 by rotating within the substantially hollow shaft 2. In particular, the driveline 30 has a proximal end that may be connected to a rotational power tool for applying torque through the driveline 30.

To accommodate the bend(s) in the substantially hollow shaft 2, the driveline 30 includes at least one universal joint. Each universal joint is located at a respective one of the bend(s). In the present example, the driveline 30 includes a universal joint 70 located at the bend 22 and a universal joint 70 located at the bend 24. An example of the universal joints will be described in more detail below in relation to FIGS. 8 and 9.

Each universal joint may be located at the interface between two driveline sections of the driveline 30. For instance, in the present example, the driveline 30 includes a distal driveline section 30A, an intermediate driveline section 30B and a proximal driveline section 30C. The distal driveline section 30A extends distally from the universal joint 70 located at the bend 22. The intermediate driveline section 30B extends between the universal joint 70 located at the bend 22 and the universal joint 70 located at the bend 24. The proximal driveline section 30C extends proximally from the universal joint 70 located at the bend 24. The proximal end of the proximal driveline section 30C may be connected to a rotational power tool for applying torque through the driveline 30 as noted above. Each driveline section may be substantially cylindrical.

The various driveline sections of the driveline may be positioned for rotation within a respective one of the shaft sections of the substantially hollow shaft 2. Each driveline section may have a longitudinal axis. The longitudinal axes of the driveline sections may be coaxially aligned with the longitudinal axes of their respective shaft sections. For instance, in the present example, the distal driveline section 30A rotates within the distal shaft section 12, the intermediate driveline section 30B rotates within the intermediate shaft section 14, and the proximal driveline section 30C rotates within the proximal shaft section 16.

As can be seen in FIGS. 1 to 7, the driveline 30 also includes a head part 40. The head part 40 of the driveline 30 extends distally from the distal end of the substantially hollow shaft 2. In the present example, the head part 40 is located at a distal end of the distal driveline section 30A. The head part 40 may have a substantially cylindrical outer surface. As can be seen in, for instance, FIGS. 1, 2A and 6, a diameter of the substantially cylindrical outer surface of the head part 40 may match a diameter of a substantially cylindrical outer surface of the distal shaft section 12, so that there is substantially no change in the outer diameter of the surgical rotational tool driver 10 at the interface between the distal end of the distal shaft section 12 and the head part 40.

Figure 2A:
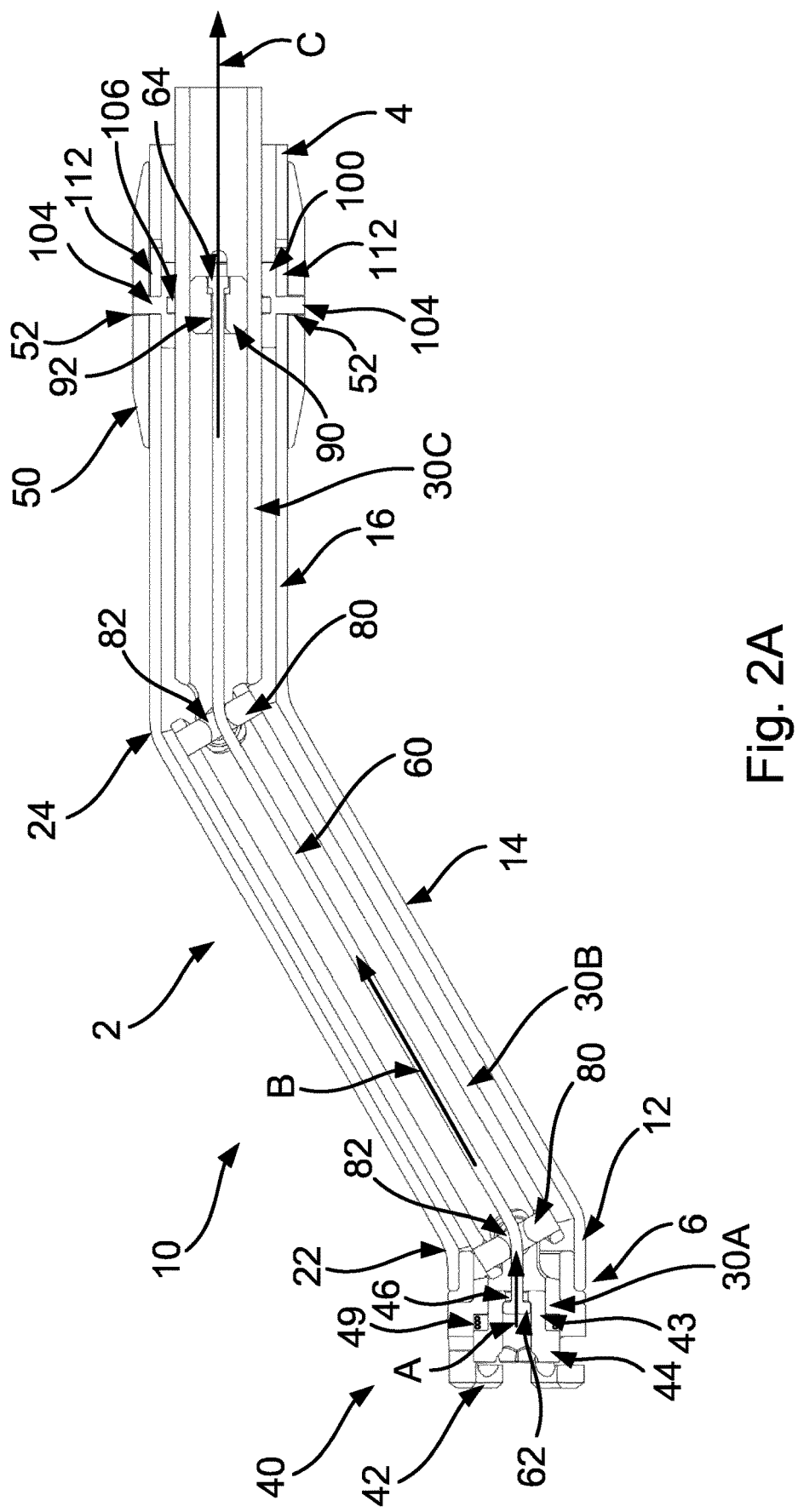
FIG. 2A shows a cross section of the surgical rotational tool driver of FIG. 1.
Figure 2B:
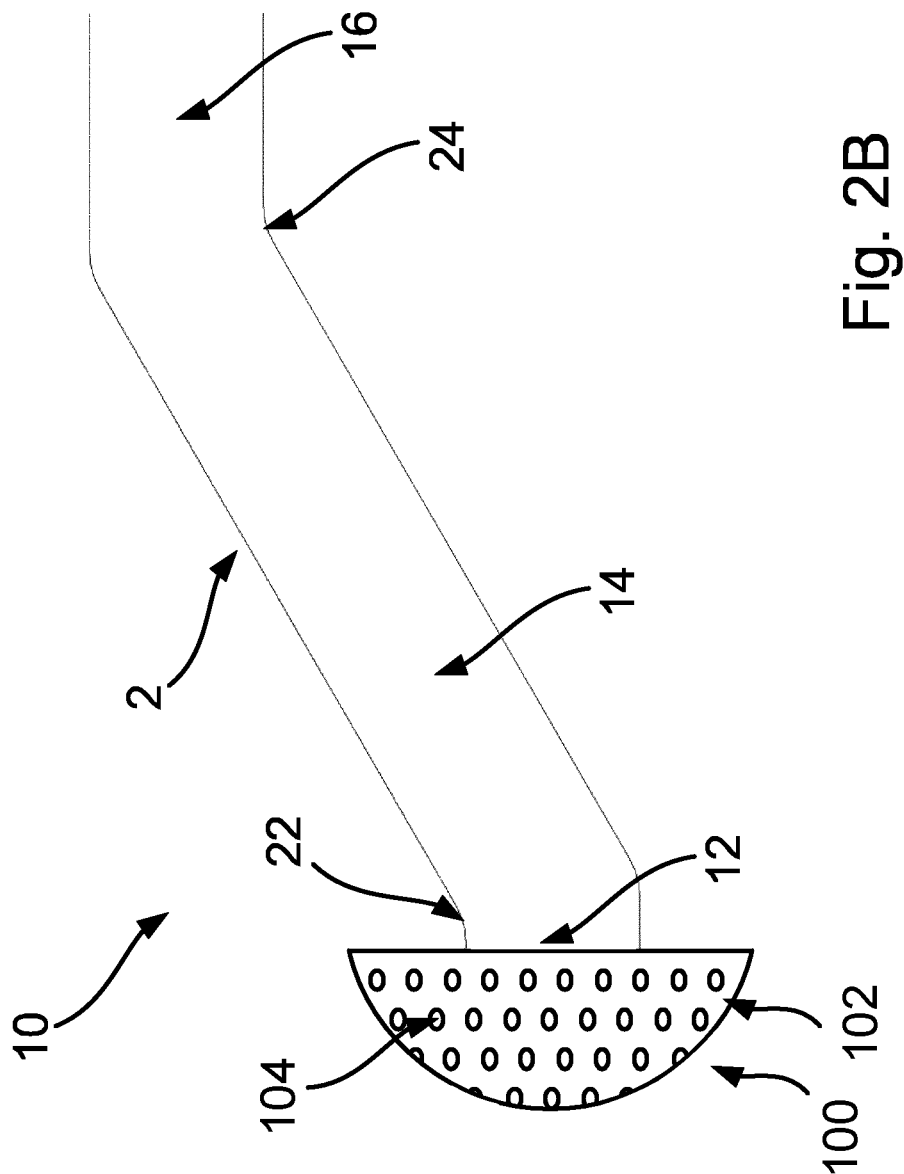
FIG. 2B shows the surgical rotational tool driver of FIG. 1 with a surgical rotational tool attached.
Figure 3:
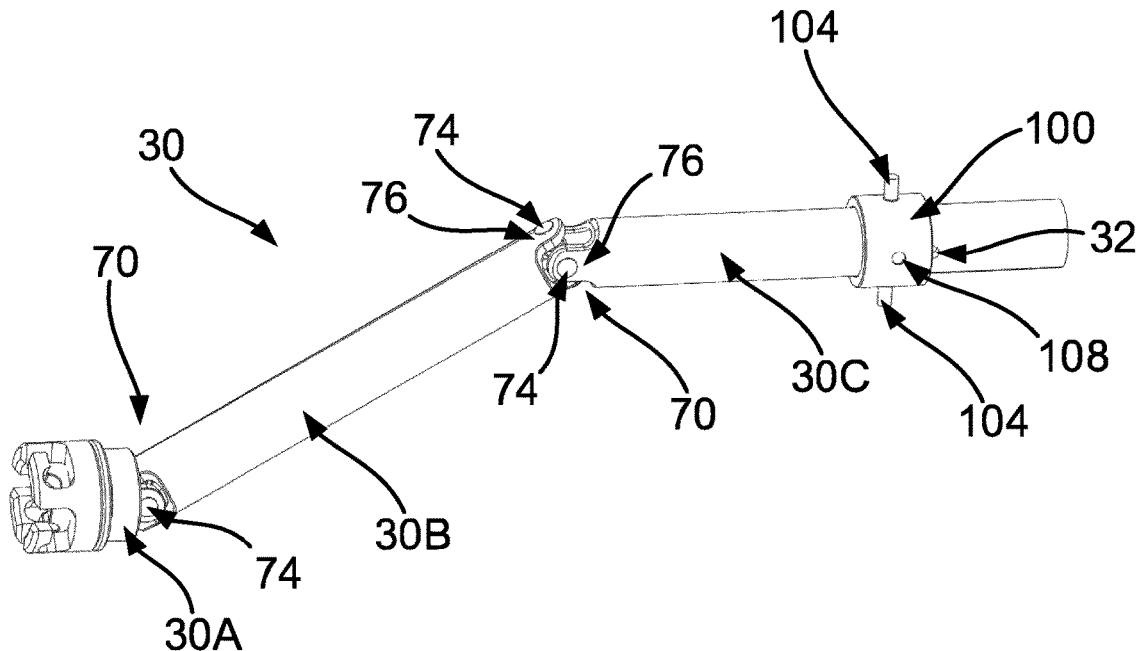
FIGS. 3 and 4 show the driveline of the surgical rotational tool driver of FIG. 1.
Figure 4:
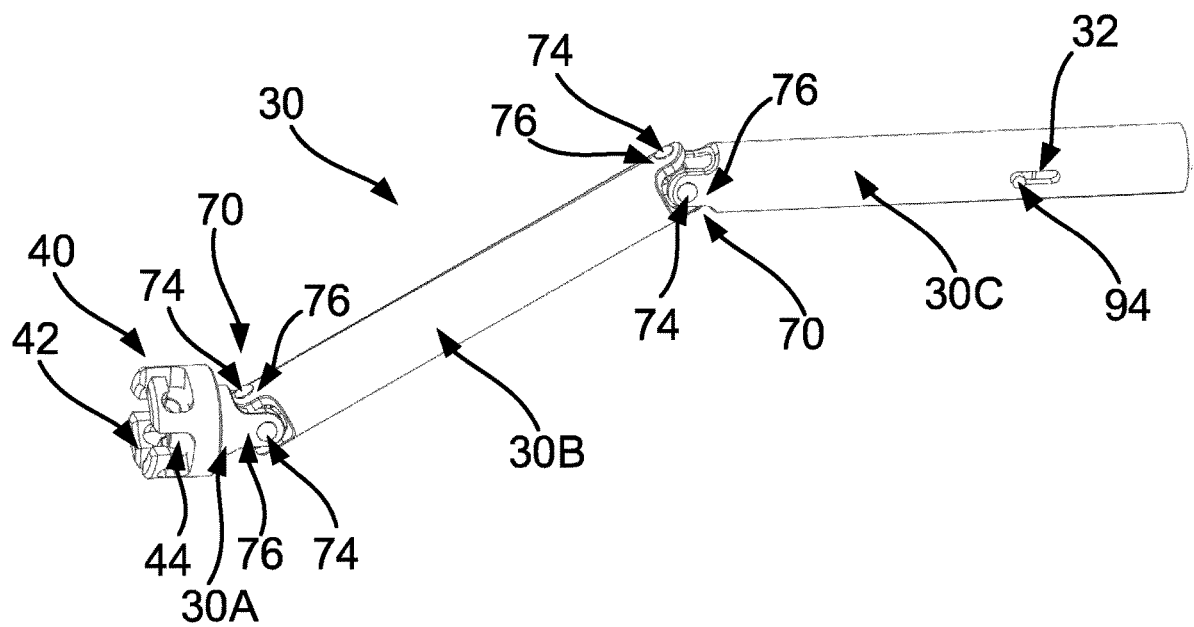
Figure 5:
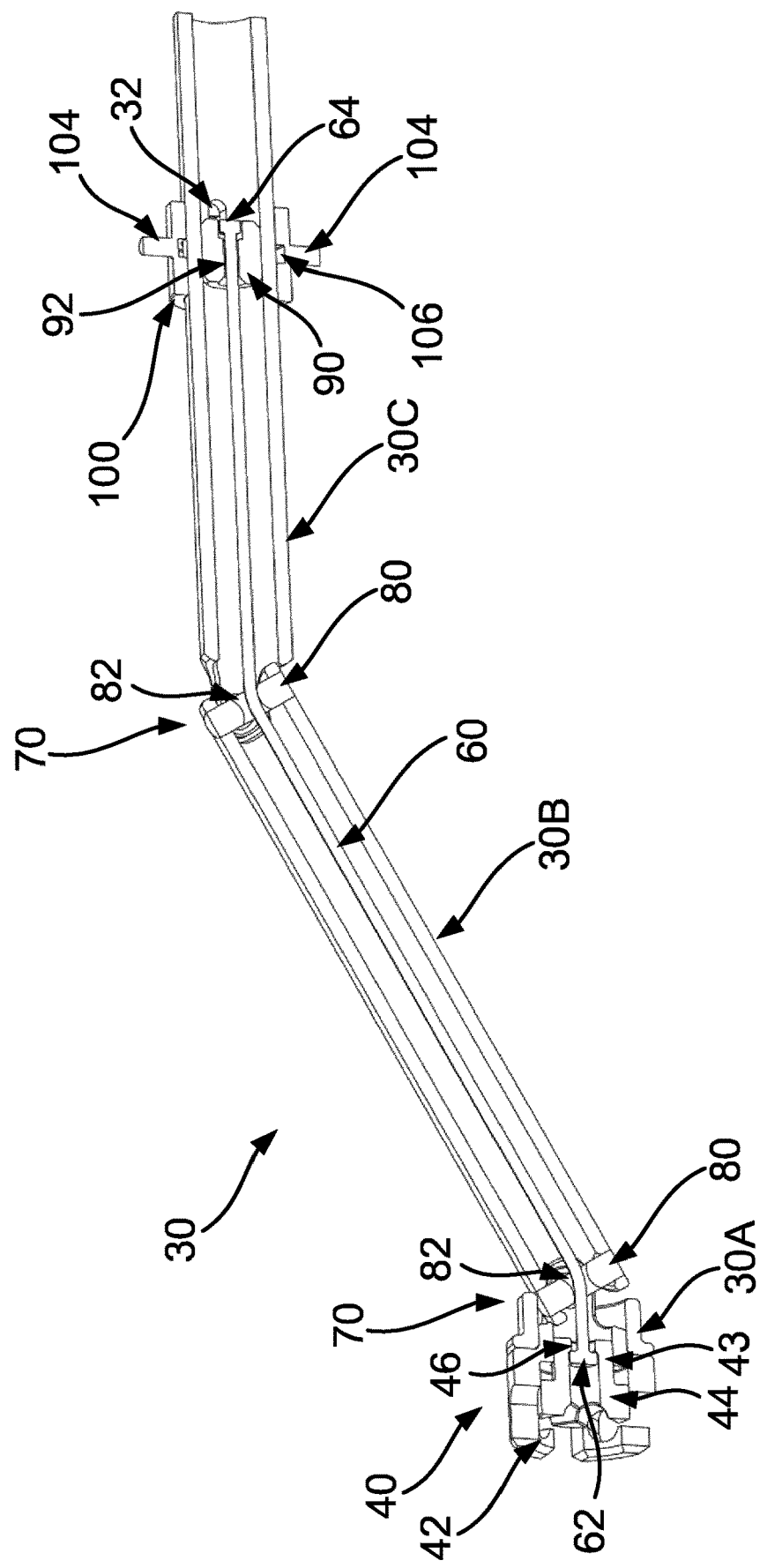
FIG. 5 shows a cross section of the driveline of the surgical rotational tool driver of FIG. 1.

The head part 40 is connectable to a surgical rotational tool. The surgical rotational tool may for instance be a reamer, such as an acetabular reamer 100 as shown in FIG. 2B. As shown in FIG. 2B, the acetabular reamer 100 may, for instance comprise a hemispherical dome 102 for insertion into the acetabulum of a patient. An outer surface of the dome 102 may include features 104 for grating bone away from the inner surface of the acetabulum as the acetabular reamer 100 rotates with the driveline 30.

To implement the connection between the head part 40 and the surgical rotational tool, the head part 40 may include distally located connection features 42 for connection with corresponding connection features of the surgical rotational tool. As shown in, for instance, FIGS. 6 and 7, the connection features 42 include a release mechanism for releasing the head part 40 from the surgical rotational tool.

In the present example, the release mechanism includes one or more teeth 44 that are receivable within openings of the corresponding connection features of the surgical rotational tool. The teeth 44 extend distally from a slideably moveable central shaft 43 of the head part 40. The central shaft 43 may be substantially cylindrical. The central shaft 43 may be located in a centrally located bore in the head part 40.

The central shaft 43 may be biased distally with respect to the other features of the head part 40 using e.g. a spring 49. The spring 49 (which may, for instance be a helical spring as shown in FIG. 2A) may be located in a space located between a distally facing surface of the head part 40 and a proximally facing surface of a flange of the central shaft 43 (see the region labelled 47 in FIG. 6).

Figure 6:
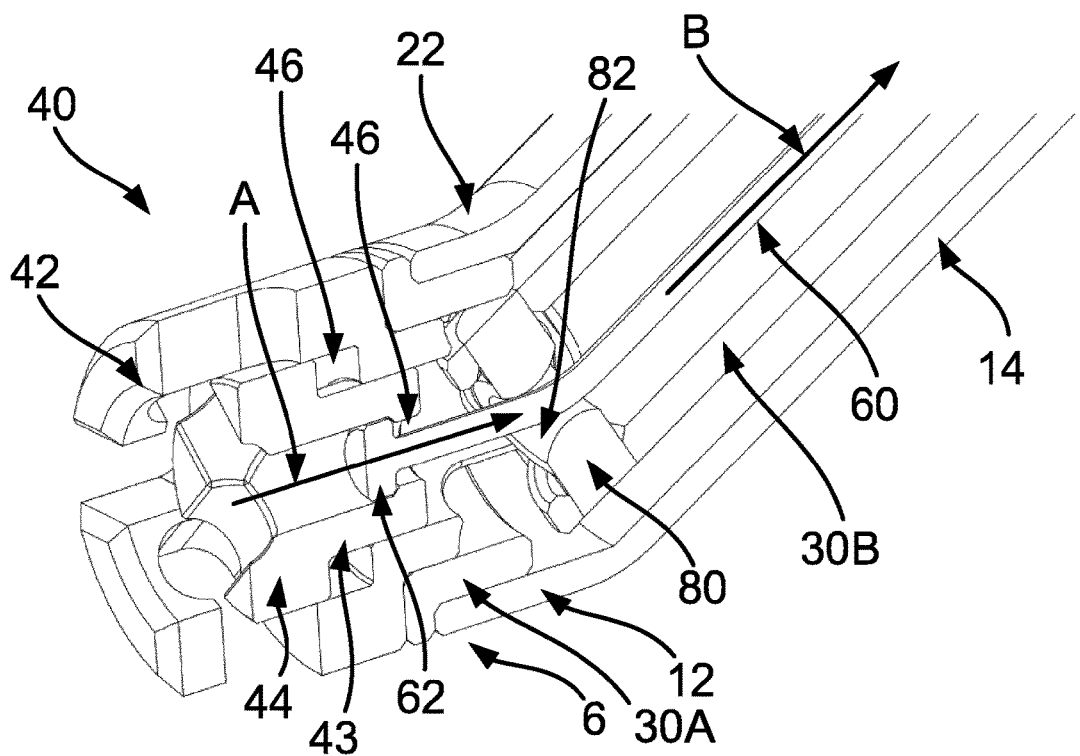
FIG. 6 shows a cross section of the distal end of the surgical rotational tool driver of FIG. 1.

As will be described in more detail below, the central shaft 43 may be withdrawn proximally (e.g. along the longitudinal axis of the distal driveline section 30A—this is illustrated by the arrow labelled A in FIG. 6) to withdraw the teeth 44 from the openings of the corresponding connection features.

As shown in, for instance, FIGS. 2A, 5, 6, 8 and 10 to 12, the surgical rotational tool driver 10 also includes an actuation member 60. As noted above, the driveline 30 is substantially hollow. The actuation member 60 extends within the substantially hollow driveline 30 (see, e.g. FIGS. 2A, 5 and 6). The actuation member 60 is connected to the release mechanism. This can allow the release mechanism to be operated remotely. In particular, because the actuation member 60 extends within the substantially hollow driveline 30, the release mechanism may be operated at a position on the surgical rotational tool driver 10 that is located proximally with respect to the head part 40.

In the present example, the release mechanism is operated by withdrawing the actuation member 60 proximally within the driveline 30. A distal end 62 of the actuation member 60 is attached to the central shaft 43, as shown in FIGS. 2A and 6. To implement the attachment of the actuation member 60 to the central shaft 43, in the present example the central shaft 43 includes a central axial bearing surface within which the actuation member 60 is rotationally received. The central axial bearing surface of the central shaft 43 includes an axial bore in the central shaft 43. The distal end of the actuation member 60 is received within and extends within the bore. The bore has a narrowed portion 46, which may be located at a proximal end of the bore. The actuation member 60 has a widened part 62, which is located distally with respect to the narrowed portion 46 of the bore.

In use, when the actuation member 60 is withdrawn proximally within the driveline 30 as noted above (see the arrows labelled A, B and C in FIGS. 2A and 6), the widened part 62 of the actuation member 60 urges against the narrowed portion 46 whereby the central shaft 43 is moved proximally (e.g. against the bias provided by the spring 49), which in turns disengages the teeth 44 from the above described openings of the corresponding connection features of the surgical rotational tool. This allows the surgical rotational tool to be released from the head part 40 of the driveline 30.

The actuation member 60 may also by withdrawn proximally while the surgical rotational tool is being mounted on the head part 40. This may allow other connection features 42 of the head part 40 and the corresponding connection features of the surgical rotational tool to be manipulated into the correct position without interference from the teeth 44 of the central shaft 43.

During rotation of the driveline 30 to transmit torque to the surgical rotational tool, it is envisaged that the driveline 30 may rotate relative to the actuation member 60. For instance, the actuation member 60 may remain substantially stationary during rotation of the driveline 30. In the present example, the distal end of the actuation member 60 is rotationally received within the bore in the central shaft 43, to allow relative rotation between the actuation member 60 and the driveline 30. The inner bearing surface of the bore, and the surface of (at least the distal end of) the actuation member 60 may be smooth, so as to reduce friction between them as the driveline 30 rotates. It is anticipated that residual friction forces between the actuation member 60 and the inner bearing surface of the bore may cause some rotation of the actuation member 60 while the driveline 30 rotates, although it is anticipated that the angular velocity of the actuation member 60 would typically be substantially lower than that of the driveline 30. Similar considerations apply to the passage of the actuation member 60 through the substantially hollow central portion of the spider part(s) to be described below. Similar considerations also apply to attachment between the actuation member 60 to the inner sleeve 90 of the actuation mechanism to be described below, to allow relative rotation between the actuation member 60 to the inner sleeve 90 during rotation of the driveline 30.

The actuation member 60 may be substantially flexible. This may allow the actuation member 60 to navigate the bend(s) 22, 24 in the substantially hollow shaft 2. In some examples, the actuation member 60 may comprise a substantially flexible tension member. The actuation member 60 may, for instance, comprise a substantially flexible wire.

The actuation member 60 may comprise a polymer. In one example, the actuation member 60 may comprise Polytetrafluoroethylene (PTFE). In another example, the actuation member 60 may comprise polyethylene. For instance, an ultra-high molecular weight polyethylene could be used (e.g. Dyneema). In a further example, the actuation member 60 may comprise poly-para-phenylene terepthalamide (Kevlar).

The actuation member 60 may, for instance, comprise an alloy. For instance, the alloy may be Nickel Titanium (Nitinol).

As noted above, the actuation member 60 extends within the substantially hollow driveline 30. As noted above, the flexible nature of the actuation member 60 can allow it to navigate the bend(s) 22, 24 in the substantially hollow shaft 2. The universal joint(s) 70 may be configured to allow the actuation member 60 to pass through it in such a way that it does not interfere with the operation of the universal joint(s) 70 during rotation of the driveline 30.

Figure 7:
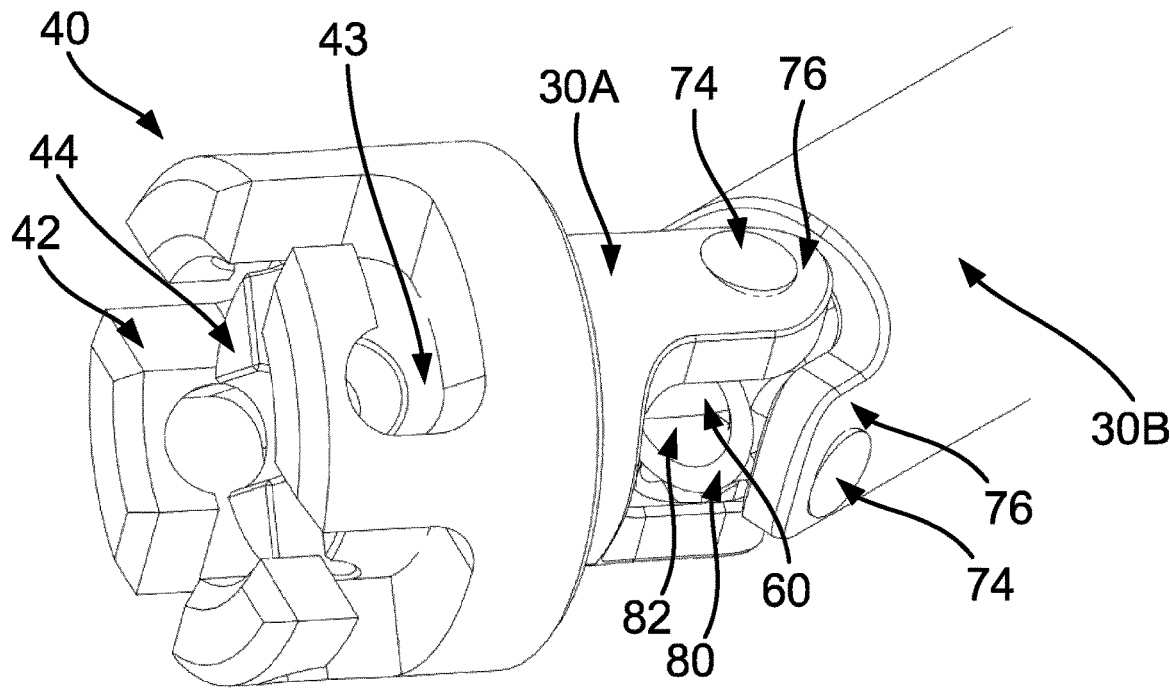
FIG. 7 shows a distal end of the driveline of the surgical rotational tool driver of FIG. 1.
Figure 8:
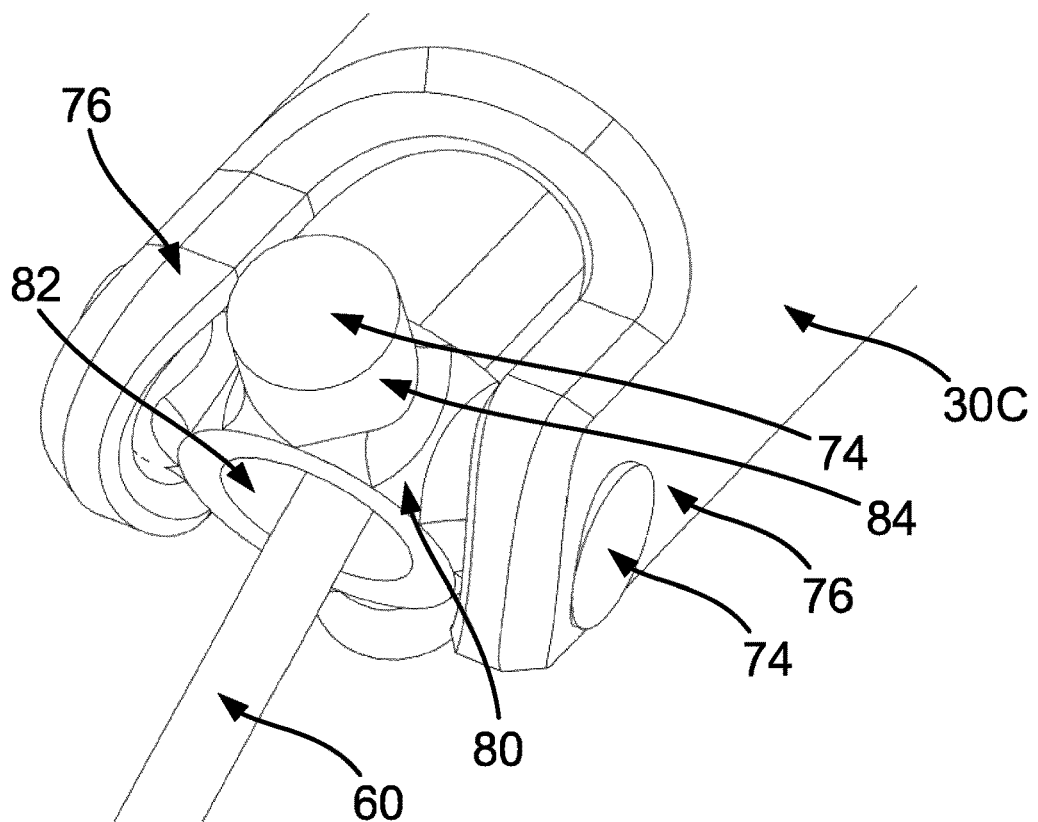
FIG. 8 shows some of the features of a universal joint of the driveline of the surgical rotational tool driver of FIG. 1.
Figure 9:
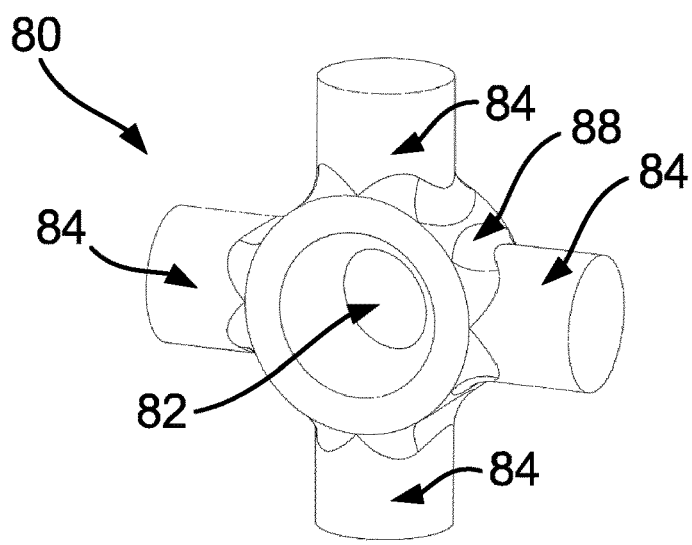
FIG. 9 shows a spider part of a universal joint of a driveline of the surgical rotational tool driver of FIG. 1.

With reference to FIGS. 7 and 8, each universal joint 70 in this example includes a pair of yokes, each yoke being located at an end of one of the two driveline sections that the universal joint 70 connects together. Each yoke includes a pair of arms 76. The arms 76 may be arranged at regular intervals around the universal joint (typically, as shown in the figures, the arms 76 of a first yoke are arranged at the 12 o'clock and 6 o'clock positions, while the arms 76 of a second yoke are arranged at the 3 o'clock and 9 o'clock positions.

The universal joint(s) 70 may include a substantially hollow central portion, through which the actuation member 60 extends. In the present example, the substantially hollow central portion is comprised of a spider part 80 (see FIG. 9).

The spider part 80 may include a body part 88. The body part 88 may be located at the center of the spider part 80. The spider part 80 may also include a number of legs 84. The legs may extend radially outward from the body part 88. The legs 84 may be circumferentially distributed around the body part 88. An end of each leg 84 is pivotally attached to one of the arms 76 of the yokes located at the ends of the driveline sections that the universal joint 70 interconnects. As shown in FIG. 8, the ends of the legs 84 may pass through openings in the arms 76 to faun pivotal connections 74. These pivotal connections allow the tilting of the driveline sections that the universal joint 70 interconnects, relative to each other, so as to allow the substantially hollow driveline 30 to navigate the bend(s) 22, 24 in the substantially hollow shaft 2.

In the present example, the spider part 80 has four legs 84, which are circumferentially distributed around the body part 88 at the 12 o'clock, 3 o'clock, 6 o'clock and 9 o'clock positions, for pivotal attachment to a respective one of the arms 76. By way of example, the pivotal attachment of two of the legs 84 of a spider part 80 to the arms 76 of a yoke provided at the proximal end of the distal driveline section 30C is shown in FIG. 8.

The spider part 80 includes an aperture 82. The aperture 82 passes though the body part 88. The aperture 82 is may be centrally located within the body part 88. The actuation member 60 extends though the aperture 82. The intermediate driveline section 30B is omitted in FIG. 8 to reveal the path of the actuation member 60 through the driveline and in particular through the aperture 82.

The provision of the aperture 82 in the body part 88 of the or each universal joint 70 of the driveline 30 can allow the actuation member 60 to extend within the substantially hollow driveline 30 while navigating the bend(s) 22, 24 in the substantially hollow shaft 2.

As mentioned above, it is envisaged that, during rotation of the driveline 30 to transmit torque to the surgical rotational tool, the driveline 30 may rotate relative to the actuation member 60. To allow this, the actuation member 60 is rotationally received within the aperture 82 in the body part 88. The inner surface of the aperture 82 and the surface of the actuation member 60 may be smooth, so as to reduce friction between them as the driveline 30 rotates. It is anticipated that residual friction forces between the actuation member 60 and the inner surface of the aperture 82 may cause some rotation of the actuation member 60 while the driveline 30 rotates, although it is anticipated that the angular velocity of the actuation member 60 would typically be substantially lower than that of the spider part 80.

In some examples, the surgical rotational tool driver 10 may include an actuation mechanism. The actuation mechanism may be located along the substantially hollow shaft 2. It is envisaged that the actuation mechanism may be located in a position that is remote from the distal end 6 of the substantially hollow shaft 2. In this position the actuation mechanism may be conveniently accessible by the surgeon. For instance, the actuation mechanism may be located outside the wound space even while the surgical rotational tool driver 10 is being used (i.e. while a surgical rotational tool attached to the head part 40 is located inside the wound space). In some examples, the actuation mechanism may be located proximally with respect to a mid-way point located equidistant the proximal end 4 and the distal end 6 of the substantially hollow shaft 2. In some examples, the actuation mechanism may be located at the proximal end of the substantially hollow shaft 2.

In the present example, the surgical rotational tool driver 10 includes an actuation mechanism that is located along the proximal shaft section 16 of the substantially hollow shaft 2. It is envisaged that the actuation mechanism may instead be located along the intermediate shaft section 14 of the substantially hollow shaft 2.

The actuation mechanism is operable to withdraw the actuation member 60 proximally within the driveline 30. As described above, the withdrawal of the actuation member 60 proximally within the driveline 30 operates the release mechanism for releasing the head part 40 from a surgical rotational tool.

Figure 10:
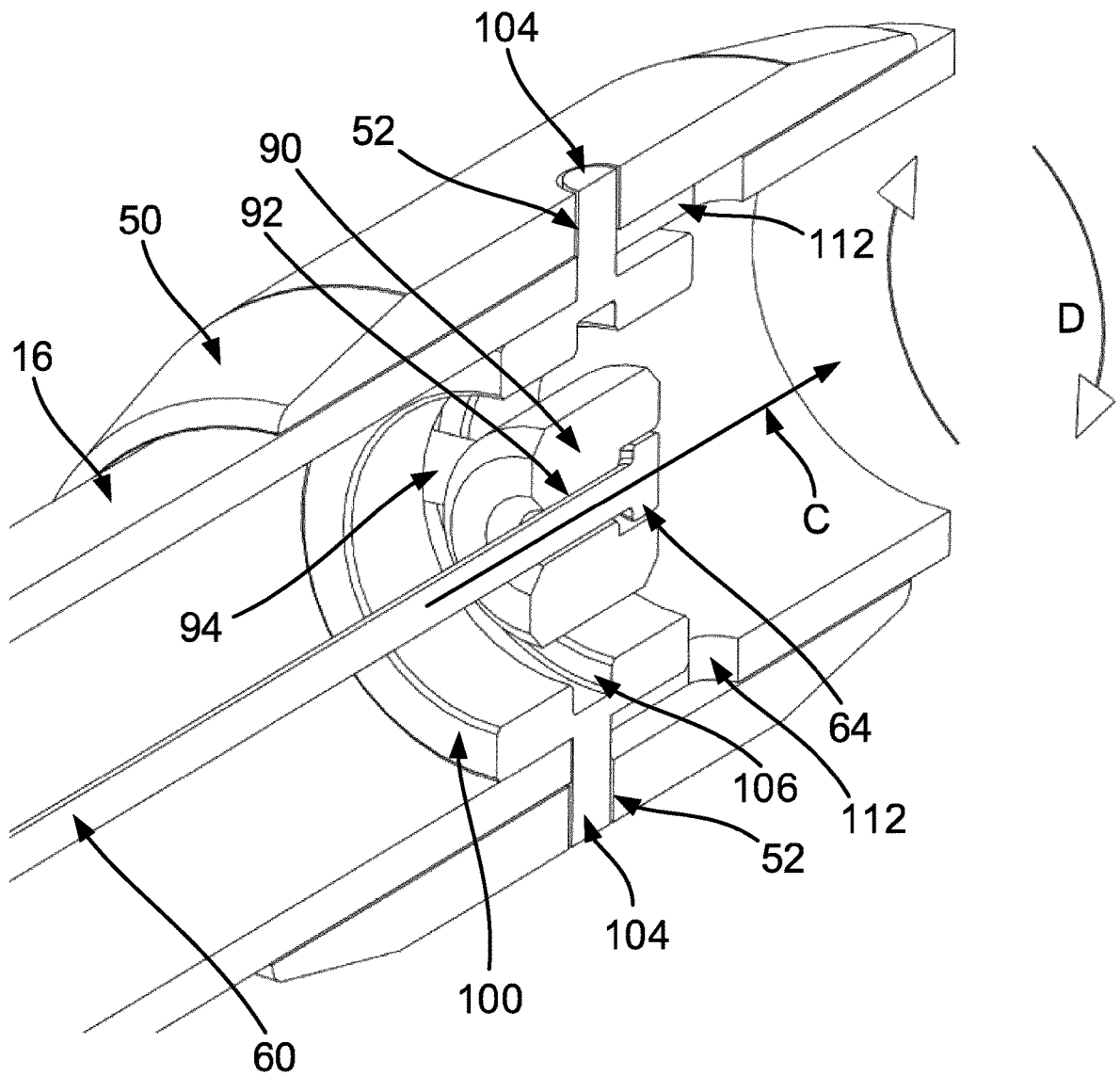
FIG. 10 shows a cross section of an actuation mechanism of the surgical rotational tool driver of FIG. 1 (the driveline is not shown in FIG. 10)
Figure 11:
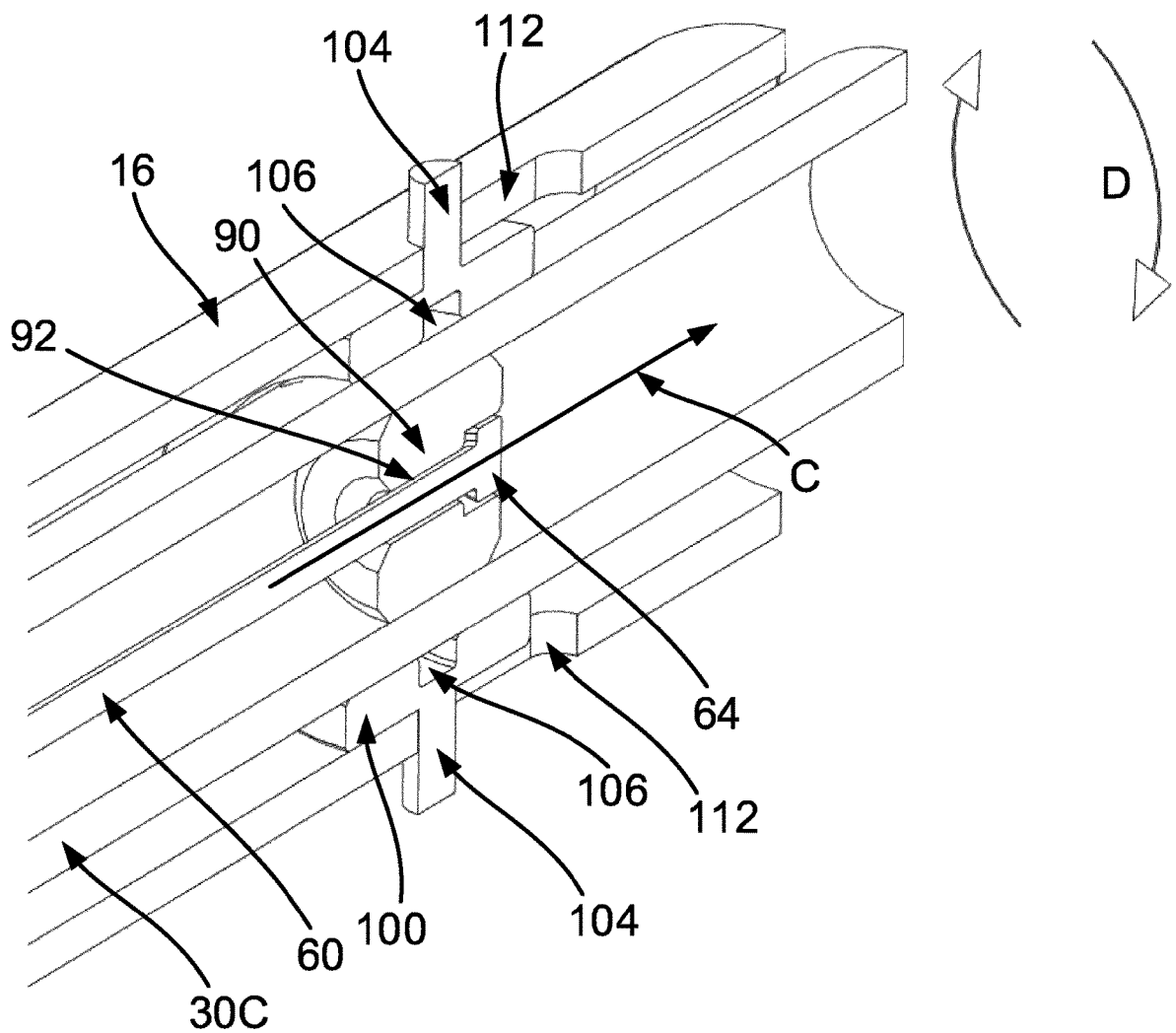
FIG. 11 shows another cross section of the actuation mechanism of the surgical rotational tool driver of FIG. 1.

The actuation mechanism of the present example will be described below with reference to FIGS. 10 to 12.

The release mechanism in this example includes an inner sleeve 90. The inner sleeve 90 may be substantially cylindrical. The inner sleeve 90 is mounted inside the proximal driveline section 30C of the driveline 30 (see FIG. 11—note that the driveline is not shown in FIG. 10 or 12, so as to reveal the inner sleeve 90, its attachment to the actuation member 60 and the interaction between the inner sleeve 90 and the intermediate sleeve 100 to be described below). The inner sleeve 90 is configured to rotate with the driveline 30 (e.g. see the arrows labelled D in FIGS. 10 and 11).

In this example, a proximal end of the actuation member 60 is attached to the inner sleeve 90. To implement the attachment of the actuation member 60 to the inner sleeve 90, the inner sleeve 90 is provided with a central opening that has an axial bearing surface within which the actuation member 60 is rotationally received. In this example, the central opening comprises a bore. The bore has a narrowed portion 92, which may be located at a proximal end of the bore. The actuation member 60 has a widened part 64, which is located proximally with respect to the narrowed portion 92 of the bore. By operating the actuation mechanism to move the inner sleeve 90 proximally, the actuation member 60 may be withdrawn in a proximal direction (see the arrow labelled C in FIG. 11) within the driveline 30 as described above.

In this example, the driveline 30 has one or more openings 32 located in a side wall thereof. The openings 32 are slot shaped, with their long dimension substantially parallel to the longitudinal axis of the proximal driveline section 30C. The inner sleeve 90 has one or more first members 94. The first members 94 may be substantially cylindrical, and may extend radially outward from an outer surface of the inner sleeve 90. The first members 94 each extend through a respective one of the opening(s) 32 located in the side wall of the driveline 30 (see also FIG. 4). Note that when the driveline 30 rotates, the inner sleeve 90 rotates with the driveline 30, owing to the engagement of the first member(s) 94 with their respective openings 32.

Each first member 94 is slideable back and forth within its respective opening 32 located in the side wall of the driveline 30, along the long dimension of the opening 32. This can allow the inner sleeve 90 as a whole to move back and forth along the longitudinal axis of the proximal driveline section 30C. When the inner sleeve 90 is moved proximally as noted above, an edge of the bore, formed by proximal end of the narrowed portion 92, urges against the widened part 64 of the actuation member 60, thereby to withdraw the actuation member 60 proximally within the driveline 30.

As described above, it is envisaged that, during rotation of the driveline 30 to transmit torque to the surgical rotational tool, the driveline 30 (and hence the inner sleeve 90) may rotate relative to the actuation member 60. For instance, the actuation member 60 may remain substantially stationary during rotation of the driveline 30 and the inner sleeve 90. To allow this, the actuation member 60 may be rotationally received within the bore in the inner sleeve 90. The inner surface of the bore in the inner sleeve 90 and the surface of the actuation member 60 may be smooth, so as to reduce friction between them as the driveline 30 and the inner sleeve 90 rotate. It is anticipated that residual friction forces between the actuation member 60 and the inner surface of the bore in the inner sleeve 90 may cause some rotation of the actuation member 60 while the driveline 30 and the inner sleeve 90 rotate, although it is anticipated that the angular velocity of the actuation member 60 would typically be substantially lower than that of the driveline 30 and the inner sleeve 90.

In this example, the actuation mechanism also comprises an intermediate sleeve 100. The intermediate sleeve 100 is mounted between an outer surface of the drive line 30 and an inner surface of the substantially hollow shaft 2. The intermediate sleeve 100 may be substantially cylindrical.

In this example, the proximal shaft section 16 has one or more openings 112 located in a side wall thereof. The openings 112 are slot shaped, with their long dimension substantially parallel to the longitudinal axis of the proximal shaft section 16. The intermediate sleeve 100 has one or more second members 104. The second members 104 may be substantially cylindrical, and may extend radially outward from an outer surface of the intermediate sleeve 100. The second members 104 each extend through a respective one of the opening(s) 112 located in the side wall of the proximal shaft section 16.

Each second member 104 is slideable back and forth within its respective opening 112 located in the side wall of the proximal shaft section 16, along the long dimension of the opening 112. This can allow the intermediate sleeve 100 as a whole to move back and forth along the longitudinal axis of the proximal shaft section 16 (which may be parallel to the longitudinal axis of the proximal driveline section 30C).

The intermediate sleeve 100 includes a central opening having an axial bearing surface within which the (proximal driveline section 30C of the) driveline 30 is rotationally received to allow rotation of the driveline 30 while the intermediate sleeve remains substantially stationary. Note that when the driveline 30 rotates, the intermediate sleeve 100 cannot rotate with the driveline 30, owing to the engagement of the second member(s) 104 with their respective openings 112.

In this example, a part of the central opening of the intermediate sleeve 100 has an increased diameter to form an inwardly facing circumferential slot 106. As can be seen in the Figures, the slot 106 may be substantially annular in shape. An outer end of the or each first member 94 of the inner sleeve 90 extending through the opening(s) 32 located in the side wall of the proximal driveline section 30C is rotationally received within the annular slot 106. This allows the inner sleeve 90 to rotate with the driveline 30 as described above, while the outer end of the or each first member 94 rides within the slot 106. On the other hand, when the intermediate sleeve 100 as a whole is moved back and forth along the longitudinal axis of the proximal shaft section 16 as noted above, the edges of the slot 106 urge against the or each first member 94, which in turn moves the or each first member 94 within its respective opening 32, whereby the inner sleeve 90 moves axially with along the intermediate sleeve 100. Accordingly, by moving the intermediate sleeve 100 in a proximal direction, the inner sleeve 90 can also be moved proximally, in turn to proximally withdraw the actuation member 60 within the driveline 30 to operate the release mechanism.

Figure 12:
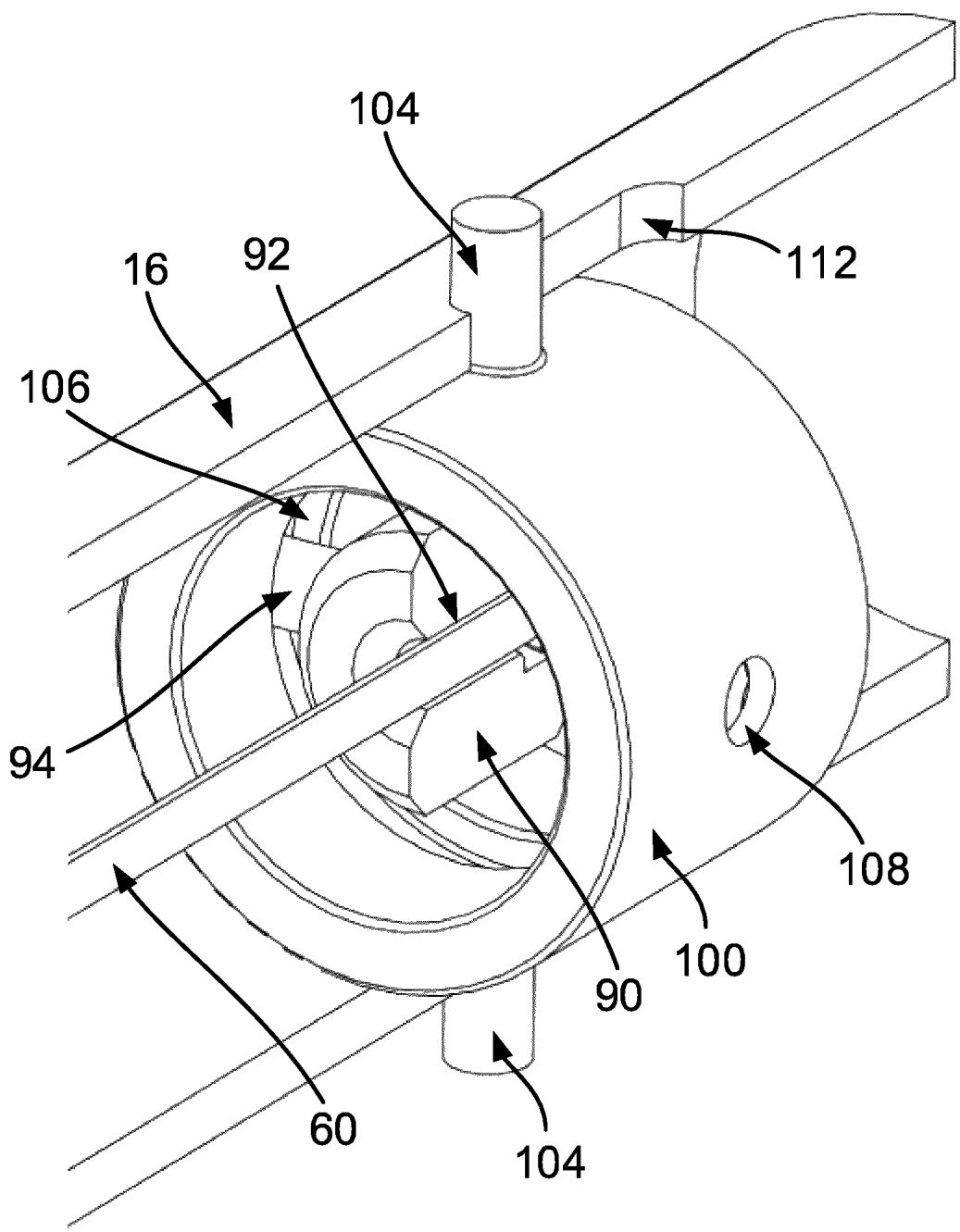
FIG. 12 shows a cut away view of the actuation mechanism of the surgical rotational tool driver of FIG. 1 (the driveline is not shown in FIG. 12)

As shown in FIG. 12, the intermediate sleeve 100 may include one or more apertures 108. The aperture(s) 108 may extend radially through the sidewall of the intermediate sleeve 100 and in this example the aperture(s) 108 open out into the slot 106. The aperture(s) 108 may allow the first members 94 to pass through them for assembly with the inner sleeve 90 during manufacture of the surgical rotational tool driver 10. The inner sleeve 90 may include one or more radially extending bores located in an outer curved (cylindrical) surface thereof, into which the first members 94 may be inserted.

In this example, the actuation mechanism further comprises an outer sleeve 50. The outer sleeve 50 is slideably mounted on an outer surface of the (proximal shaft section 16 of the) substantially hollow shaft 2. The outer sleeve 50 may be substantially cylindrical. Proximal and/or distal ends of the outer sleeve 50 may be tapered in towards longitudinal axis of the proximal shaft section 16, to provide the surgical rotational tool driver 10 with a smooth profile.

In this example, the outer sleeve 50 is connected to the or each second member 104. In particular, the outer ends of each of the second member(s) 104 may extend radially outward through the opening(s) 112, to be received in a respective opening 52 located in the outer sleeve 50 (e.g. see FIG. 10). The openings 52 of the outer sleeve 50 within which the second member(s) 104 are received may be shaped to conform with the outer surfaces of the second member(s) 104, so as to form a press fit between the openings 52 and the second member(s) 104.

The connection of the outer sleeve 50 to the second member(s) 104 allows the outer sleeve 50 to be moved back and forth along the longitudinal axis of the proximal shaft section 16 thereby the move intermediate sleeve 100 axially. As described above, this in turn moves the inner sleeve 90 axially, so that the actuation member 60 can be withdrawn proximally to operate the release mechanism.

The outer sleeve 50 thus provides the surgeon with a means by which to manually operate the actuation mechanism, which in turn operates the release mechanism as described above. It is envisaged that in examples in which the central shaft 43 is biased distally (e.g., by the spring 49), when the surgeon releases outer sleeve 50, each of the inner sleeve 90, the intermediate sleeve 100 and the outer sleeve 50 may return to a locking position of the actuation mechanism under the tension in the actuation member 60. This locking position may thus be a default position of the actuation mechanism. A release position of the actuation mechanism may be reached by manually moving the outer sleeve 50 (and thus the inner sleeve 90 and the intermediate sleeve 100) proximally.

A method of operating a surgical rotational tool driver 10 of the kind described above may include connecting the one or more connection features 42 of the head part 40 of the substantially hollow driveline 30 to a surgical rotational tool. As noted previously, this may involve withdrawing the actuation member 60 proximally (e.g. by operating the release mechanism), to allow connection features 42 of the head part 40 and the corresponding connection features of the surgical rotational tool to be manipulated into the correct position without interference from the teeth 44 of the central shaft 43.

The surgical rotational tool may, for example, be an acetabular reamer driver of the kind shown in FIG. 2B.

Having attached the surgical rotational tool to the surgical rotational tool driver 10, the method may then include applying torque through the driveline 30. This may involve connecting a rotational power tool to the proximal end of the driveline 30 as noted above, and then operating the rotational power tool.

The method may also include operating the release mechanism described above to release the head part 40 from the surgical rotational tool by withdrawing the actuation member 60 proximally within the driveline 30.

Figure 13:
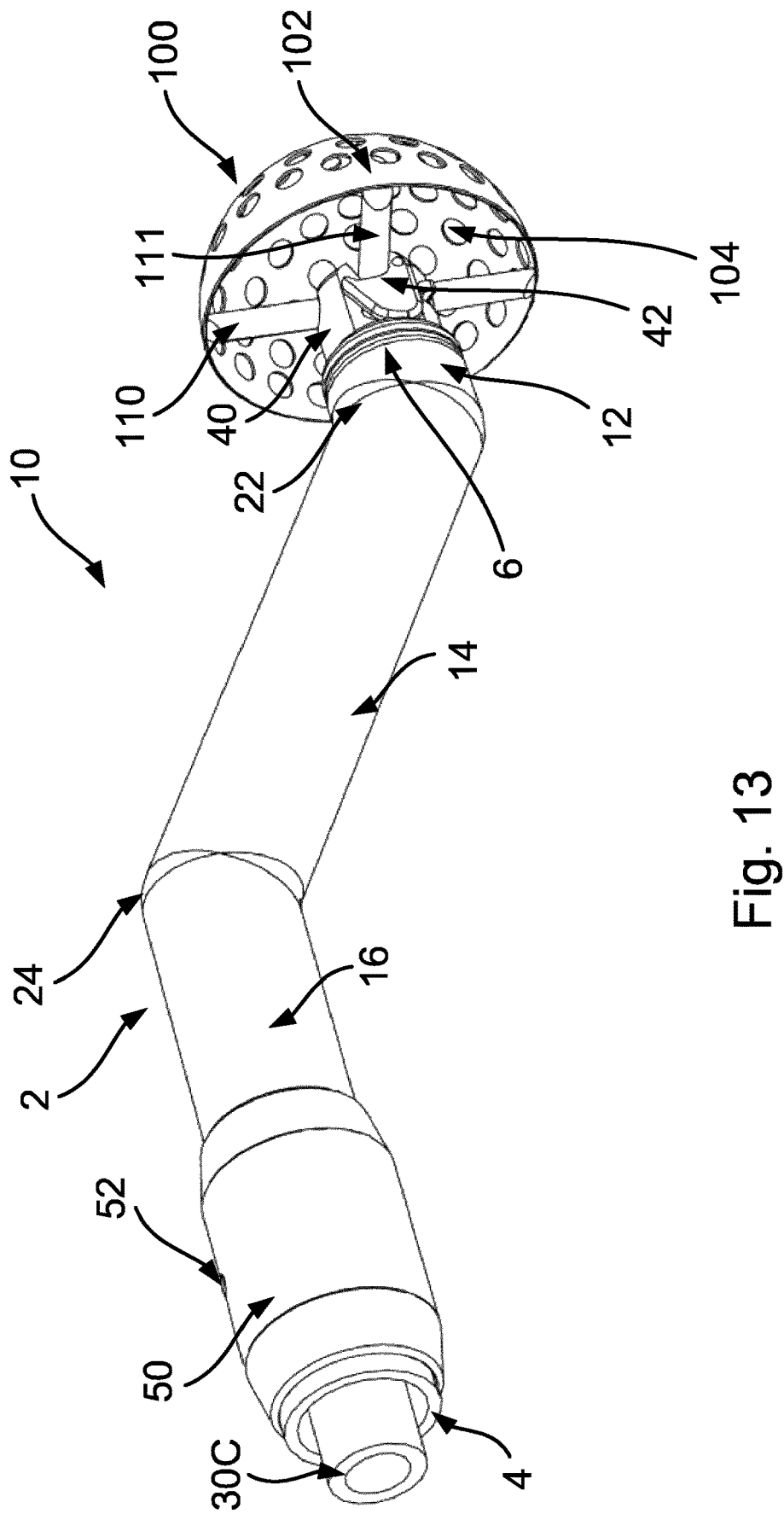
FIG. 13 shows a surgical rotational tool driver according to another embodiment of the invention.

FIGS. 13 to 25 show a surgical rotational tool driver 10 according to another embodiment of the invention. In particular, FIG. 13 shows the surgical rotational tool driver 10 of the present embodiment, FIGS. 14A to 14C illustrate the attachment of a surgical rotational tool (such as an acetabular reamer 100) to the surgical rotational tool driver 10, and FIGS. 15 to 25 show the connection features of the surgical rotational tool driver 10.

The surgical rotational tool driver 10 has a number of components in common with the embodiments described above in relation to FIGS. 1 to 12. In particular, the components of the surgical rotational tool driver 10 located proximally with respect to the distal shaft section 12 shown in, for example, FIG. 13, may be the same as described above in relation to FIGS. 1 to 12. However, the head part 40 of the embodiment described below in relation to FIGS. 13 to 25 differs from the head part 40 described in relation to the embodiment of FIGS. 1 to 12. The head part 40 and its operation will now be described in detail herein below.

The head part 40 extends distally from the distal end 6 of the substantially hollow shaft 2 of the surgical rotational tool driver 10. In the present example, the head part 40 is located at a distal end of the distal driveline section 30A. The head part 40 is operable to rotate around an axis of rotation 201 (see FIG. 16) under the torque transmitted to the head part 40 by the driveline 30.

The head part 40 has a housing 200 the housing 200 may have a substantially cylindrical outer surface 202, which is curved about the axis of rotation 201 of the head part 40. The head part 40 may also have a pair of substantially flat outer lateral surfaces 248. The lateral surfaces 248 may be provided on opposite lateral sides of the head part 40 and may separate two curved sections 202A, 202B (see FIG. 16) of the substantially cylindrical outer surface 202 from each other.

Figure 15:
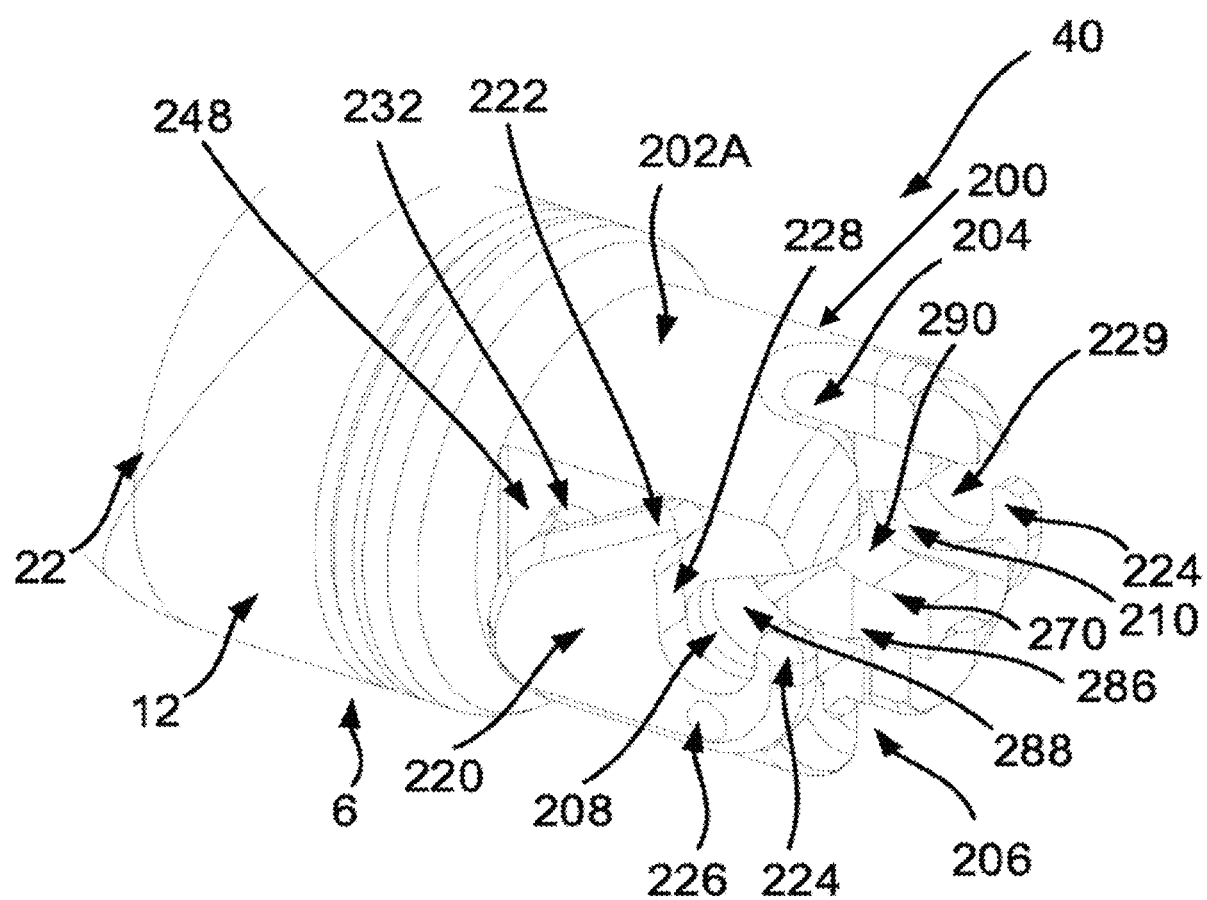
FIGS. 15 to 25 show the connection features of the surgical rotational tool driver of FIG. 13.
Figure 16:
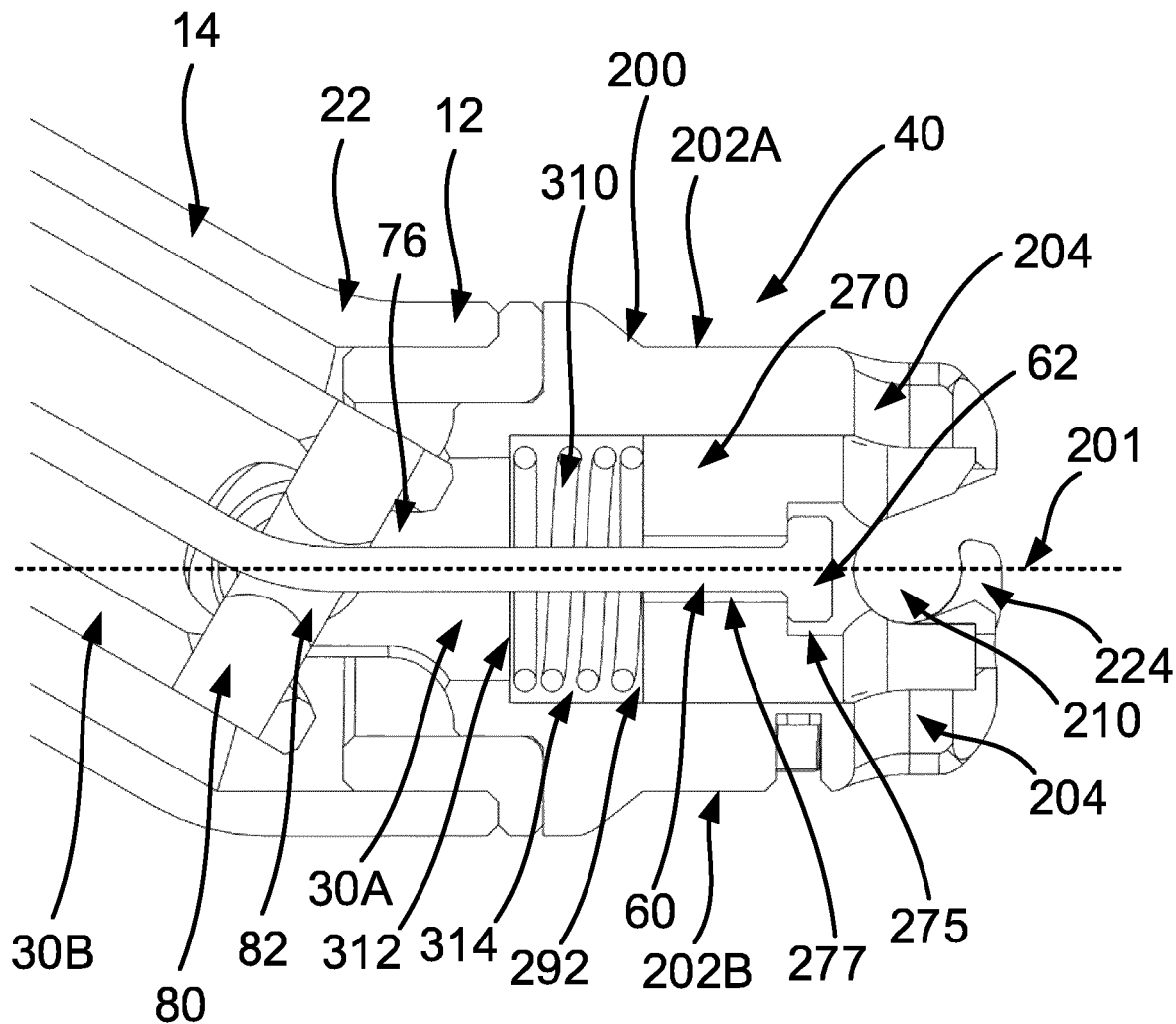
Figure 17:
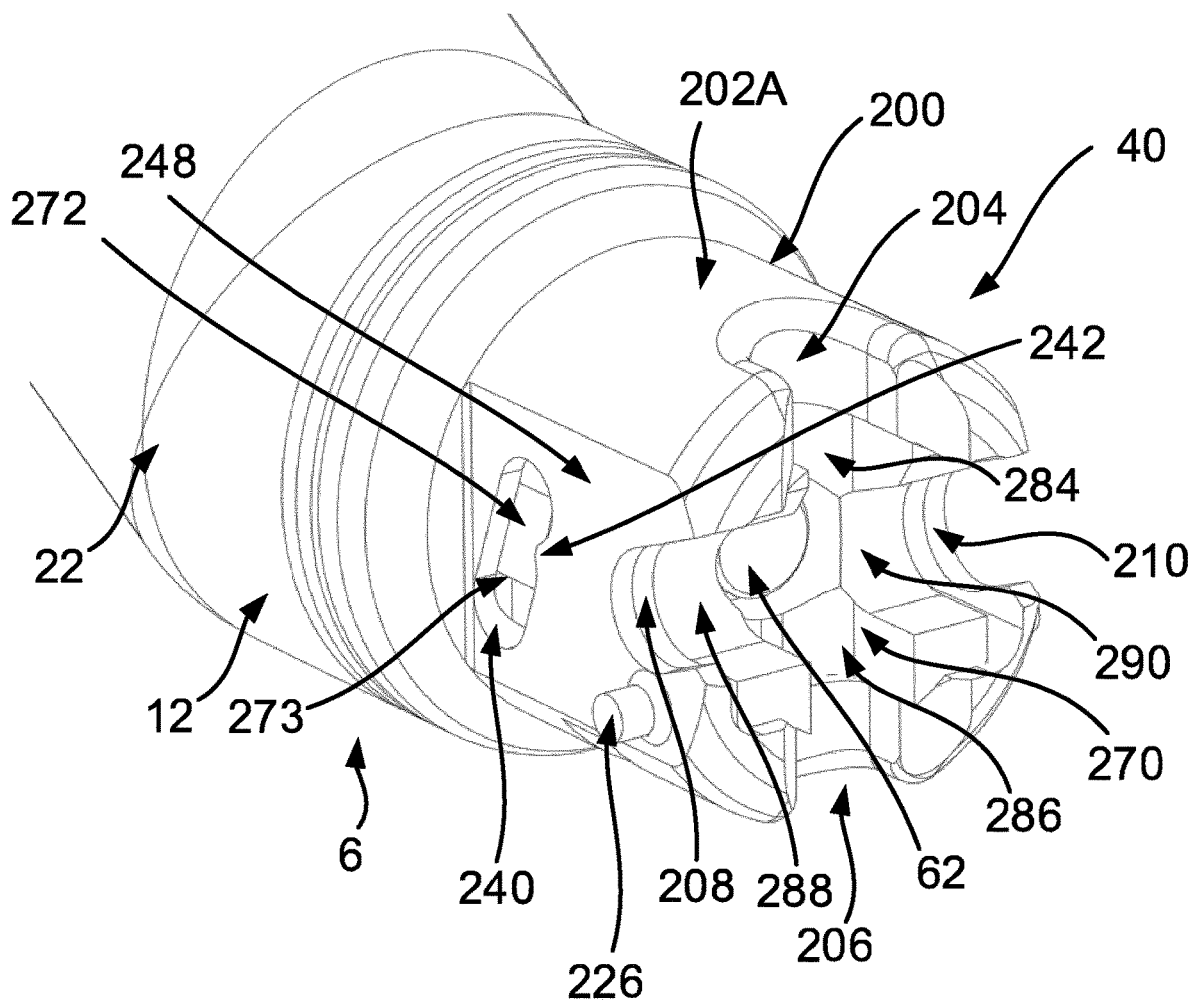
Figure 18:
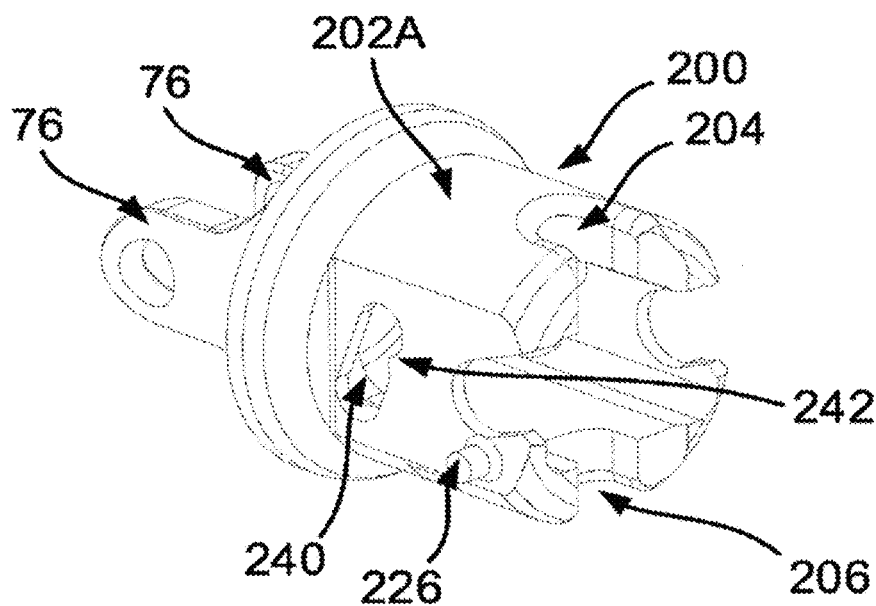

As can be seen in, for instance, FIGS. 15 and 16, a diameter of the substantially cylindrical outer surface 202 of the head part 40 may be smaller than a diameter of a substantially cylindrical outer surface of the distal shaft section 12. The pair of substantially flat lateral surfaces 248 may also be located inside the locus of the substantially cylindrical outer surface of the distal shaft section 12. The can allow space for the jaw members 220 described below to be accommodated.

The head part 40 is connectable to a surgical rotational tool. The surgical rotational tool may for instance be a reamer, such as an acetabular reamer 100 as shown in FIGS. 13 and 14A-C. As shown in FIG. 13, the acetabular reamer 100 may, for instance comprise a hemispherical dome 102 for insertion into the acetabulum of a patient. An outer surface of the dome 102 may include features 104 for grating bone away from the inner surface of the acetabulum as the acetabular reamer 100 rotates with the driveline 30.

To implement the connection between the head part 40 and the surgical rotational tool, the head part 40 includes a number of connection features for connection with the corresponding connection features of the surgical rotational tool. The connection features of the surgical rotational tool may comprise one or more members 110, 111. In the present embodiment, the connection features of the surgical rotational tool include two member 110, 111 which extend across a proximal end of the surgical rotational tool. The members 110, 111 are arranged at right angles to each other. The connection features of the head part 40 include a release mechanism for releasing the head part 40 from the surgical rotational tool 100. The connection features of the head part 40 will now be described in detail.

The connection features of the head part include a pair of jaw members 220. Each jaw member 220 may be located adjacent a respective one of the substantially flat outer lateral surfaces 248 of the housing 200. Each jaw member 220 includes a pair of jaws 222, 224 defining a space 229 for receiving the connection member 111 of the surgical rotational tool. The housing 200 also includes further spaces 208, 210 for receiving the connection member 111 and two further spaces 204, 206 for receiving the connection member 110. Each space 204, 206, 208, 210 is defined by a respective pair of jaws (e.g. see FIG. 17, which shows the head part 40 with the jaw members 220 removed). Note that the spaces 208 and 210 are substantially aligned with the spaces 229 defined by the jaws 222, 224 of the jaw members 220, whereby the connection member 111 of the surgical rotational tool can be received within both the spaces 208, 210 and the spaces 229 when the surgical rotational tool is connected to the head part 40.

Each jaw member 220 is pivotally mounted on the housing 200. In this embodiment, the each substantially flat outer lateral surface 248 of the housing 200 includes a laterally extending post 226 and each jaw member includes a bore 227 within which one of the laterally extending posts 226 is received. This allows each jaw member 220 to rotate about an axis that is substantially perpendicular to the axis 201 of rotation of the head part 40. The jaw members 220 are each rotatable between a first position (e.g. see FIGS. 14A and 24) in which the connection member 111 of the surgical rotational tool can be introduced into the spaces 229 defined by the pairs of jaws 222, 224, and second position (e.g. see FIGS. 14C, 15 and 25) in which the connection member 111 is retained within the spaces 229 defined by the jaws 222, 224 of each jaw member 220, thereby to prevent removal of the surgical rotation tool from the surgical rotational tool driver 10. As will be described below, each pair of jaws 222, 224 includes a substantially flat, inner surface 228, against which the connection member 111 may urge as it is introduced into the spaces 229, thereby to cause the jaw members 220 to rotate between the first position and the second position.

FIGS. 14A to 14C illustrate the positions of the jaw members 220 at various stages in the connection of the surgical rotation tool (in this example an acetabular reamer 100) to the surgical rotational tool driver 10.

In a first stage, shown in FIG. 14A, the jaw members 220 are initially in the first position noted above. In the first position, the spaces 229 defined by the pairs of jaws 222, 224 are presented distally, to allow the connection member 111 of the surgical rotational tool to be inserted into the spaces by moving the surgical rotational tool driver 10 toward the proximal end of the surgical rotational tool. Note that as the connection member is introduced into the spaces 229, the optional connection member 110 may also be introduced into the spaces 204, 206 defined in the housing 200.

In a next stage, shown in FIG. 14B, as the head part 40 continues to move toward the surgical rotational tool, the connection member 111 begins to urge against the substantially flat inner surface 228 of the jaw members 220. This causes the jaw members to begin to rotate about the pivot points defined by the posts 226, toward the second position.

Figure 19:
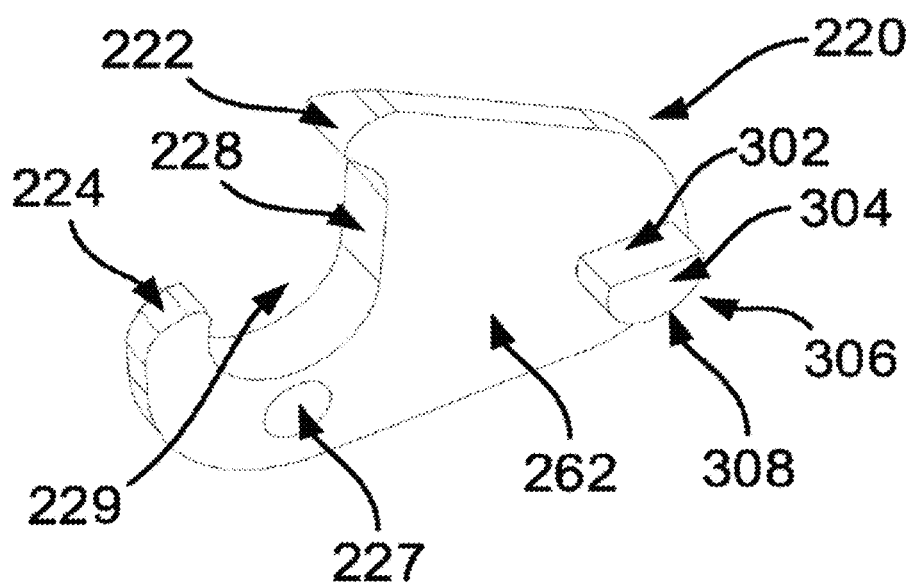
Figure 20:
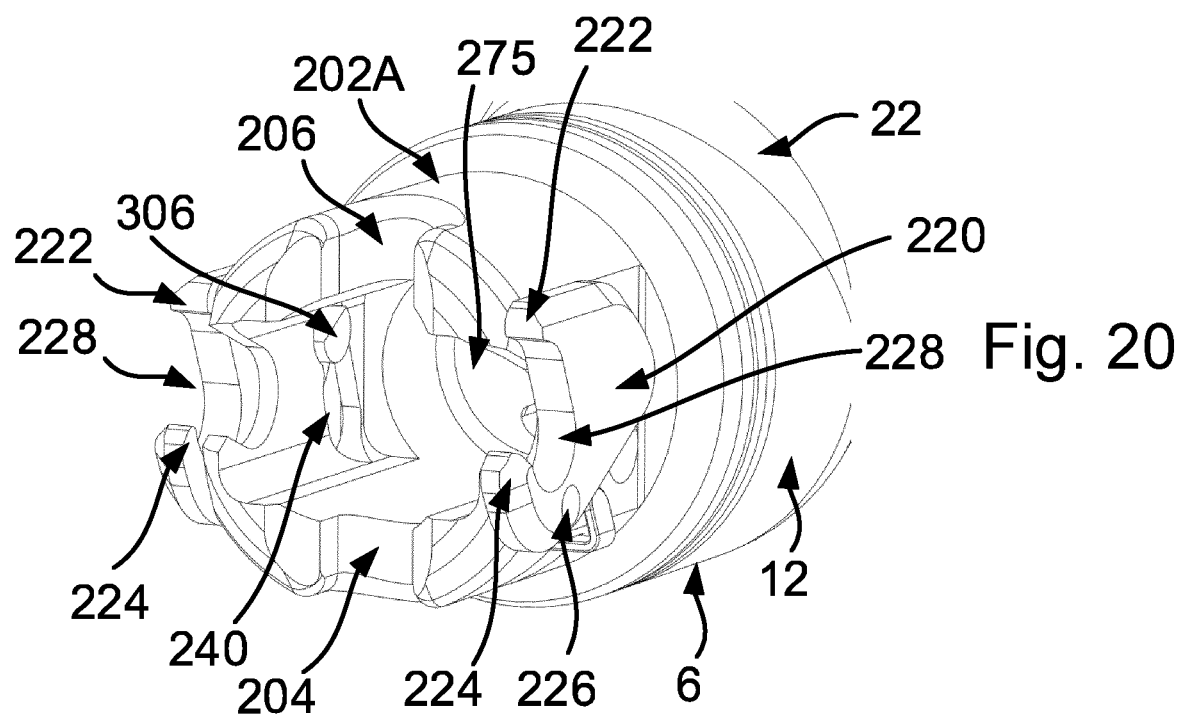

In a next stage, shown in FIG. 14C, the jaw members 220 reach the second position. With reference to FIG. 19, it is noted that the jaw 224 of each jaw member 220 is curved around an axis parallel to the axis of rotation of each jaw member 220. Because of this, when the jaw members 220 are in the second position, the ends of the jaws 224 are positioned so as to block movement of the connection members 111 in the distal direction. This prevents removal of the connection member 111 from the spaces 229, thereby preventing disconnection of the surgical rotational tool from the surgical rotational tool driver 10.

In some embodiments, the jaw members 220 may be resiliently biased toward the first position. An example of this approach will now be described with reference to FIGS. 14A-C, 24 and 25. In this example, a biasing element is mounted on the housing 200. The biasing element may comprise an elongate leaf spring 260 having a middle section 260A and two ends 260B. The middle section 260A of the leaf spring 260 may be located in a laterally extending slot provide in the curved surface 260B of the housing 200. The ends 260B may be angled to extend toward the jaw members 220. In the first position (e.g. see FIG. 24), the jaw members 220 may rest against the jaw members 220. As the jaw members 220 begin to rotate toward the second position as described above in relation to FIG. 14A-C, the jaw members urge against the ends 260B of the leaf spring 260, causing the middle section 260A to bend, thereby to resist the rotation of the jaw members 220. This biasing of the jaw member 220 toward the first position may assist in returning the jaw members to the first position, for subsequent removal of the connection member 111 form the spaces 229, during disconnection of the surgical rotational tool from the surgical rotational tool driver 10.

The surgical rotational tool driver 10 also has a locking mechanism. This locking mechanism can lock the jaw members 220 in the second position when the connection member 111 is received as shown in FIG. 14C. This can prevent the inadvertent removal of the connection member 111 from the spaces 229 during use of the surgical rotational tool. Note that while the jaw members 220 are locked in the second position, the jaw members 220 are prevented from returning to the first position under the action of the optional biasing element described above.

The locking mechanism of the present embodiment will now be described with reference to FIGS. 16-20.

The locking mechanism in this embodiment includes a release member 270. The release member 270 is located in a cavity defined by the housing 200. The release member 270 is slideably moveable within the housing 200. In particular, and with reference to FIG. 16, the release member 270 is slideable in a distal/proximal direction along the axis of rotation 201. The release member 270 may be arranged coaxially with the housing 200 for rotation about the axis 201 with the housing 200. The release member 270 is biased distally by a biasing element such as a helical spring 310. The biasing element may be located in the cavity defined by the housing, at a proximal position with respect to the release member 270. The biasing element may urge against a proximal end 292 of the release member 270 and against a lip 312 provided at a proximal end of the cavity defined by the housing 200, thereby to bias the release member 270 in the distal direction.

In the present embodiment, the release member 270 is operated by withdrawing the actuation member 60 proximally within the driveline 30. A distal end 62 of the actuation member 60 is attached to the release member 270, as shown in, for example, FIG. 16. To implement the attachment of the actuation member 60 to the release member 270, in the present example the release member 270 includes a central axial bearing surface within which the actuation member 60 is rotationally received. The central axial bearing surface of the release member 270 includes an axial bore 275 in the release member 270. The distal end of the actuation member 60 is received within and extends within the bore 275. The bore 275 has a narrowed portion 277, which may be located at a proximal end of the bore 275. The actuation member 60 has a widened part 62, which is located distally with respect to the narrowed portion 277 of the bore 275. Note that, in common with the embodiment described above in relation to FIGS. 1 to 12, the head part 40, including the release member 270, is operable to rotate under the action of the driveline 30, while the actuation member 60 remains substantially stationary.

In use, when the actuation member 60 is withdrawn proximally within the driveline 30 as noted above (see the arrows labelled A, B and C in FIGS. 2A and 6), the widened part 62 of the actuation member 60 urges against the narrowed portion 277 whereby the release member 270 is moved proximally (e.g. against the bias provided by the biasing element (e.g. the helical spring 310)).

The release member 270 may include jaw parts 276, 278 for defining spaces 284, 286, 288, 290. The spaces 288, 290 are axially aligned with the spaces 208, 210 and with the spaces 229, thereby to accommodate the connection member 111 when the connection member 111 is received within the spaces 208, 210, 229. The spaces 284, 286 are axially aligned with the spaces 204, 206, thereby to accommodate the connection member 110 when the connection member 110 is received within the spaces 204, 206.

The release member 270 includes two laterally facing, substantially flat outer surfaces 274 provided on opposite sides of the release member 270. Each surface faces toward a respective one of the jaw members 220. Each surface is provided with a ramp 271. Each ramp 271 includes a ramped surface 272 and an edge that forms a retaining surface 273 at one end of the ramped surface 272. The ramped surfaces 272 rise at an oblique angle from the substantially flat outer surfaces 274 upon which the ramps 271 are located. The ramp 271 may form a wedge shape. With reference to FIGS. 19, an inwardly facing surface 262 of each jaw member 220 includes a catch 306, which extends inwardly toward the release member 270. Each catch 306 has a ramp engaging surface 304, a rounded surface 308 and a locking surface 302. The locking surface may extend substantially orthogonally with respect to the ramp engaging surface 304. As can be seen from, for example, FIG. 20, each catch 306 extends through an opening 240 in one of the substantially flat outer lateral surfaces 248 of the housing 200. This allows the catches 306 of the jaw members 220 to interact with the ramps 271 of the release member 270. This interaction will now be described with reference again to FIGS. 14A-C, 17, and 19-21.

Figure 21:
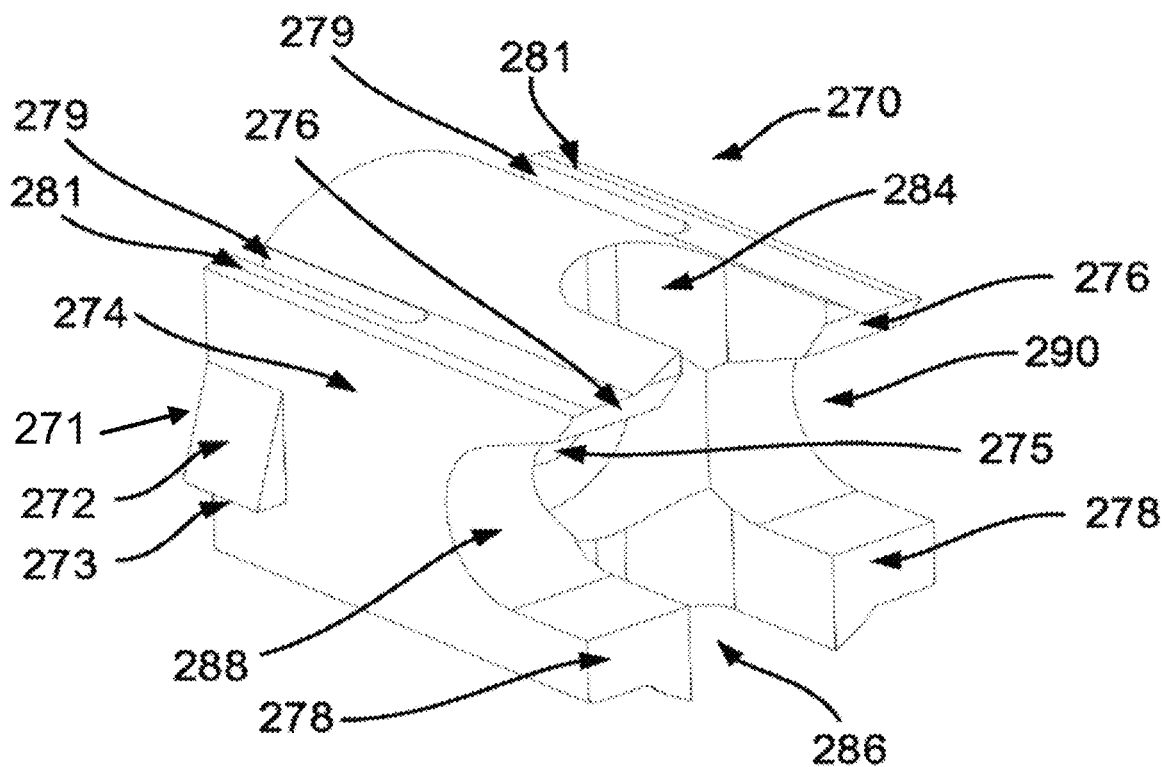

When the jaw members 220 are in the first position (FIG. 14A), the ramp engaging surface 304 rests at the bottom of the ramp. As the jaw members 220 begin to rotate from the first position to the second position (FIG. 14B), the ramp engaging surfaces 304 of each catch 306 begins to ride along the ramped surfaces 272. As can be seen in FIG. 21, the release member 270 comprises two cantilevered parts 281 formed by undercuts 279. The ramps are located on the cantilevered parts. As the ramp engaging surfaces 304 of each catch 306 ride along the ramped surfaces 272, this deflects the ramps, and consequently also the cantilevered parts 281 inward, toward the axis 201. The cantilevered parts 281 resiliently resist this inward deflection and urge outwardly against the catches 306. When the ramp engaging surfaces 304 reach the ends of the ramped surfaces 272, the cantilevered parts 281 are longer restrained by the inward pressure of the catches 306, and return to the non-deflected position shown in FIG. 21. At this point, in which the jaw members 220 have now reached the second position (FIG. 14C) the locking surfaces 302 of each catch 306 engage with the retaining surfaces 273 located at an ends of ramped surfaces 272. This prevents the jaw members 220 from moving from rotating away from the second position (e.g. under the biasing force provided by the optional biasing element (e.g. leaf spring 260) described above. Accordingly, the ramps form catches, for engaging with a respective catch 306 of each jaw member 220 to lock the jaw members 220 in the second position.

Figures 22, 23:
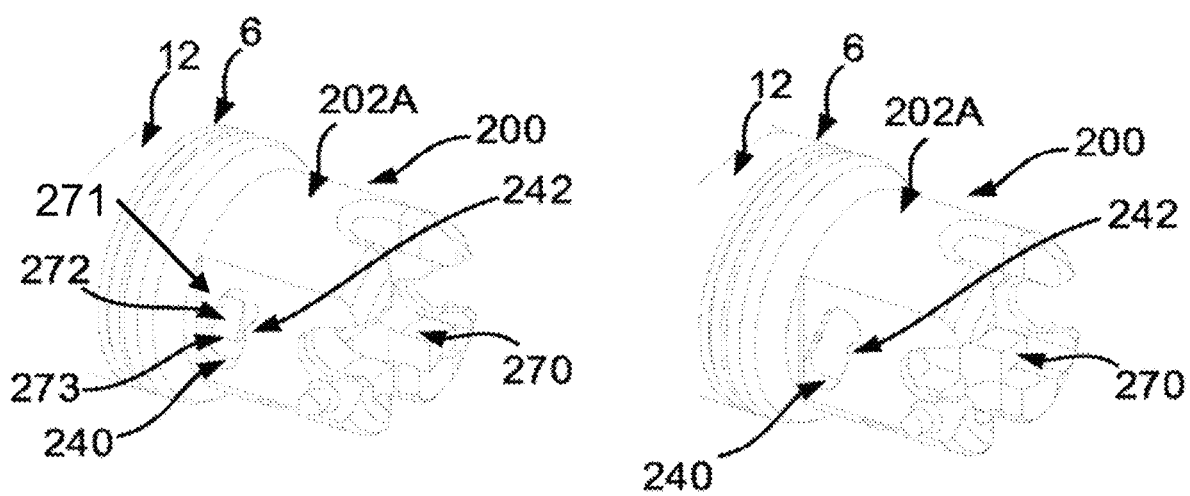
Figure 24:
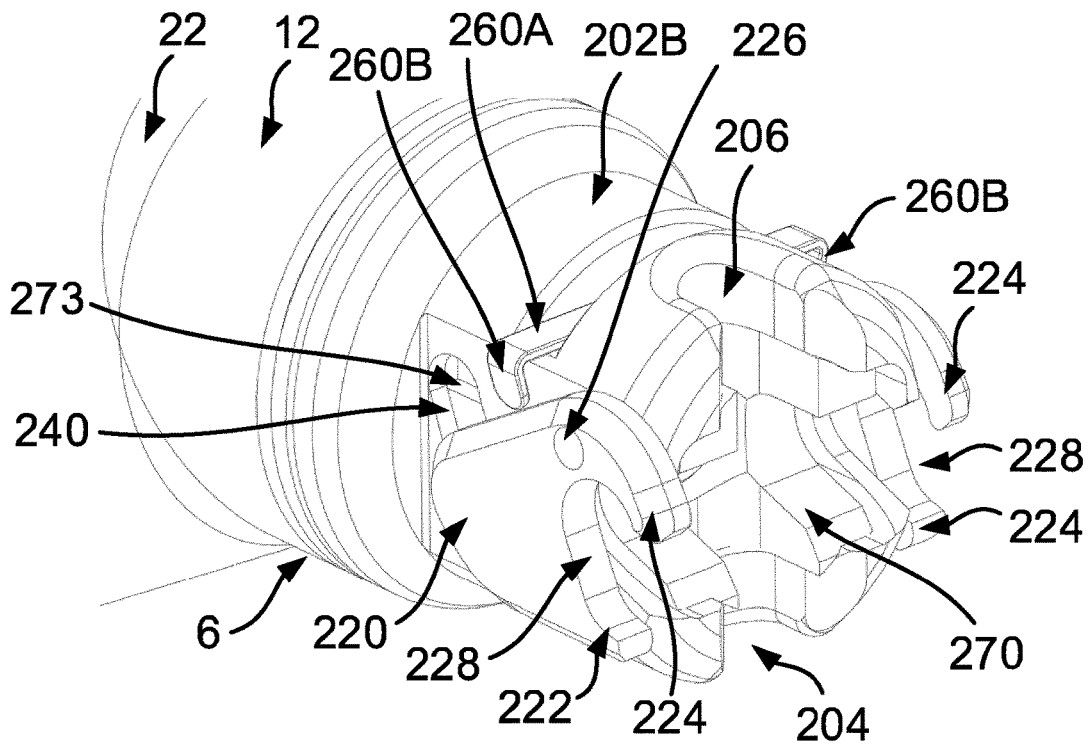
Figure 25:
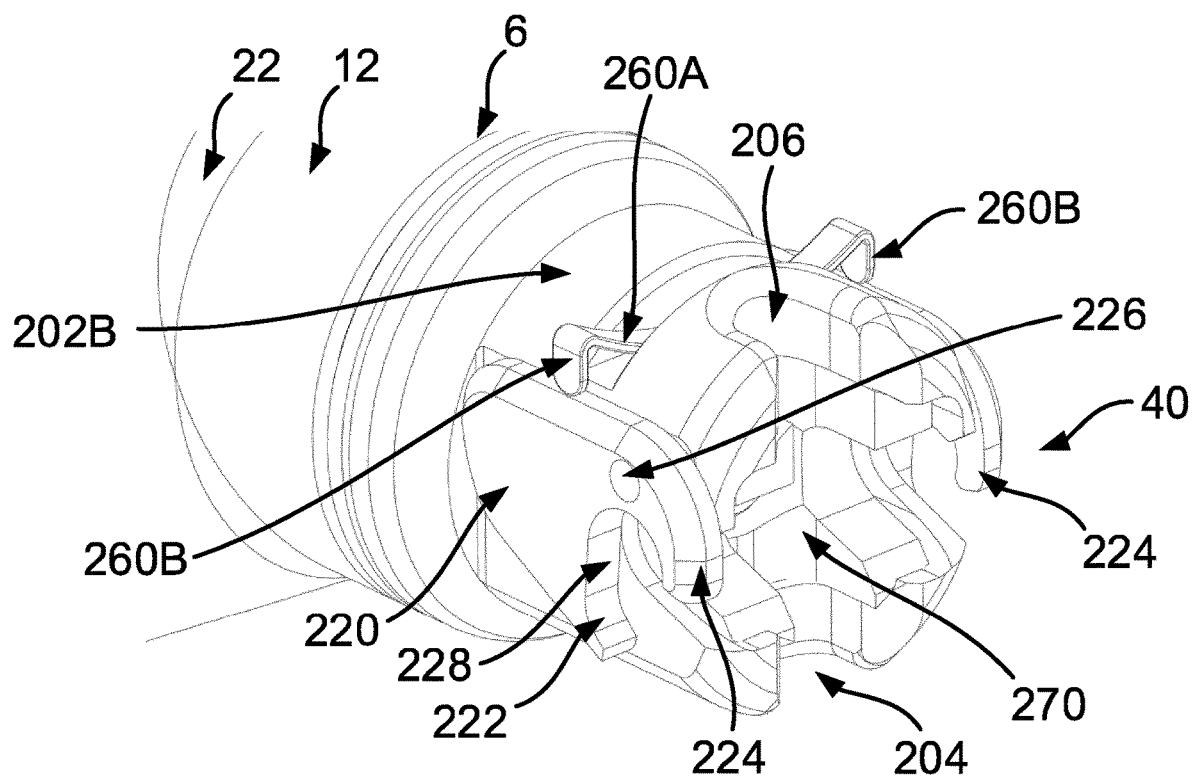

To release the jaw members 220 from the second position for disconnecting the surgical rotational tool from the surgical rotational tool driver 10, the actuation member 60 may be withdrawn proximally within the driveline 30 as described above. This may be achieved using the features of actuation mechanism described above in relation to FIGS. 10-12 (as mentioned previously, the components of the surgical rotational tool driver 10 located proximally with respect to the distal shaft section 12 shown in, for example, FIG. 13, may be the same as described above in relation to FIGS. 1 to 12). The proximal withdrawal of the actuation member 60 causes the release member 270 to slide proximally, against the bias provided by the biasing element (e.g. helical spring 310) in the housing 200. With reference to FIG. 22 (which shows the housing 200 and the release member 270 with the release member 270 in its non-withdrawn, resting position) and FIG. 23 (which shows the housing 200 and the release member 270 with the release member 270 in its withdrawn position), this has the effect of moving the ramp proximally so that the locking surface 302 of the each catch 306 disengages from the retaining surface 273 of its respective ramp. With the locking surfaces 302 disengaged from the retaining surface 273, the jaw members 220 are free to rotate back to the first position (e.g. under the biasing force provided by the biasing element (e.g. leaf spring 260)). This allows the connection member 111 to be released from the spaces 229 defined by the jaws 222, 224, thereby allowing disconnection of the surgical rotational tool from the surgical rotational tool driver 10.

With reference to FIGS. 17 to 20, it is noted that an edge of the openings 20 may each include a detent 242. The detent 242 may be located on distally located edge of each opening 20. This optional detent 242 may be provided in some embodiments, for the purpose of retaining the jaw members 220 in the first position for receipt of the connection member 111 within the jaws of each jaw member 220, prior to the attachment of the surgical rotational tool to the surgical rotational tool driver 10. This may ensure that the surgical rotational tool driver 10 is ready to be connected to the surgical rotational tool during use.

In particular, the detent 242 can serve to prevent inadvertent rotation of the jaw members 220 away from the first position (i.e. prior to the receipt of the connection member 111 within the spaces 229 defined by the jaws 222, 224) by providing a barrier to the free movement of the catches 306 of the jaw members 220 within the openings 20.

The detents 242 may be shaped and configured (e.g. made relatively shallow) such that the forces applied to the jaw members 220 when the connection member 111 is received within the spaces 229 (e.g. as the connection member 111 urges against the substantially flat inner surface 228) allows the catches 306 to overcome the detents 242, allowing the jaw members 220 to rotate into the second position as described previously.

The detents 242 may for instance be provided in embodiments that do not include the previously discussed biasing element (e.g. elongate leaf spring 260) for biasing the jaw members toward the first position. However, and as shown in the figures, it is envisaged that the detents 242 may also be present in in embodiments that do include the biasing member.

A surgical rotational tool driver according to an embodiment of this invention may be included in a surgical kit. The kit may also include one or more differently sized acetabular reamers 100 connectable to the head part of the driveline of the surgical rotational tool driver.

A method of operating a surgical rotational tool driver 10 of the kind described above in relation to FIGS. 13 to 25 includes connecting the connection features of the head part 40 of the driveline 30 of the surgical rotational tool driver 10 to a connection member (e.g. 110 and/or 111) of the surgical rotational tool (which may be an acetabular reamer 100 as noted above). The method also includes operating the release mechanism by sliding the release member 270 within the housing 200. As described above, this may include withdrawing the actuation member 60 proximally within the driveline 30. The method further includes removing the surgical rotational tool from the surgical rotational tool driver 10.

The method may also include riding the catches 306 of the jaw members 220 along the respective ramped surfaces 272 extending laterally from the release member 270 as the jaw members 220 pivot from the first position to the second position and engaging the catches 306 of the jaw members 220 with retaining surfaces 273 located at an ends of the respective ramped surfaces 272 when they reach the end of the respective ramped surfaces 272, to lock the jaw members 220 in the second position.

The method may further include sliding the release member 270 (e.g. by withdrawing the actuation member 60 proximally within the driveline 30) within the housing 200 to disengage the catches 306 of the jaw members 220 from the retaining surfaces 273 of the respective ramped surfaces on the release member 270.

The method may also include sliding the release member 270 along a direction substantially parallel to the axis of rotation 201 of the head part 40.

Accordingly, there has been described a surgical rotational tool driver and method. The driver includes a driveline extending within a hollow shaft and a head part including connection features for connecting to a connection member of a surgical rotational tool. The connection features of the head part include a housing and a pair of jaw member each including jaws for receiving the connection member. Each jaw member is pivotally mounted for rotation between: a first position for receipt of the connection member and a second position for retaining the connection member. The connection features of the head part further include a locking mechanism including a pair of catches for engaging with a respective catch of each jaw member to lock the jaw members in the second position. The locking mechanism also includes a release member slideably moveable within the housing to release the catches of the locking mechanism from the catches of the jaw members.

Although particular embodiments of the invention have been described, it will be appreciated that many modifications/additions and/or substitutions may be made within the scope of the claimed invention.

The invention claimed is:
1. A surgical rotational tool driver comprising:
a substantially hollow shaft having a proximal end and a distal end;
a driveline extending within the hollow shaft, the driveline having:

a proximal end connectable to a rotational power tool for applying torque through the driveline; and
a head part extending distally from the distal end of the shaft, the head part including connection features for connecting to a connection member of a surgical rotational tool, the head part having an axis of rotation for rotation of the surgical rotational tool on rotation of the driveline, the connection features of the head part comprising:
a housing;
a pair of jaw members, each jaw member including a pair of jaws for receiving the connection member of the surgical rotational tool, wherein each jaw member is pivotally mounted on the housing for rotation about an axis substantially perpendicular to the axis of rotation of the head part between:
a first position for receipt of the connection member within the jaws of each jaw member; and
a second position for retaining the connection member within the jaws of each jaw member to prevent removal of the surgical rotation tool from the surgical rotational tool driver; and
a locking mechanism comprising:
a pair of ramps for engaging with a respective catch of each jaw member to lock the jaw members in the second position,
a release member slideably moveable within the housing to release the ramps of the locking mechanism from the respective catches of the jaw members to allow the jaw members to return to the first position for removal of the surgical rotational tool from the surgical rotational tool driver; and
a biasing element mounted on the housing for biasing the jaw members toward the first position, wherein the biasing element includes a leaf spring having a first end for biasing a first of the jaw members and a second end for biasing a second of the jaw members.

2. The surgical rotational tool driver of claim 1, wherein the ramps of the locking mechanism each comprise:
a ramped surface extending laterally from the release member; and
a retaining surface located at an end of the ramped surface,
wherein the catches of the jaw members are operable to ride along the ramped surface as the jaw members pivot from the first position to the second position and engage with the retaining surfaces when they reach the end of the ramped surface to lock the jaw members in the second position.

3. The surgical rotational tool driver of claim 2, wherein the release member is slideably moveable within the housing to disengage the catches of the jaw members from the retaining surfaces of the ramps on the release member.

4. The surgical rotational tool driver of claim 3, wherein the release member is slideably moveable along a direction substantially parallel to the axis of rotation of the head part.

5. The surgical rotational tool driver of claim 2, wherein the housing includes an opening through which the catches of the jaw members engage with the ramped surface and the retaining surface of the ramps on the release member.

6. The surgical rotational tool driver of claim 1, wherein the locking mechanism further comprises a biasing element located within the housing for biasing the release member along the axis of rotation of the head part in a distal direction.

7. The surgical rotational tool driver of claim 1, wherein the release member includes at least one distally facing recess for receiving the connection member of the surgical rotational tool.

8. The surgical rotational tool driver of claim 1, wherein the driveline is substantially hollow, and wherein the locking mechanism further comprises an actuation member extending within the substantially hollow driveline, wherein a distal end of the actuation member is attached to the release member, and wherein the actuation member is connected to the release mechanism for operating the release member from a position on the surgical rotational tool driver located proximally with respect to the head part.

9. The surgical rotational tool driver of claim 8, wherein the substantially hollow shaft has at least one bend and wherein the driveline has a universal joint located at each said bend in the shaft.

10. The surgical rotational tool driver of claim 9, wherein the or each universal joint includes a substantially hollow central portion through which the actuation member extends.

11. The surgical rotational tool driver of claim 10, wherein the or each universal joint connects an end of a driveline section of the driveline to an end of another driveline section of the driveline and comprises:
a spider part pivotally attached to said end of each driveline section; and
an aperture in the spider part,
wherein the actuation member extends though the aperture.

12. The surgical rotational tool driver of claim 8, wherein the actuation member comprises a substantially flexible tension member.

13. The surgical rotational tool driver of claim 1, wherein the surgical rotational tool driver is a reamer driver.

14. The surgical rotational tool driver of claim 13, wherein the surgical rotational tool is an acetabular reamer.

15. A surgical kit comprising a surgical rotational tool driver according to claim 1 and a surgical rotational tool having said connection member.

16. A method of operating a surgical rotational tool driver, the method comprising:
connecting one or more connection features of a head part of a driveline of a surgical rotational tool driver to a connection member of a surgical rotational tool, the surgical rotational tool driver comprising:
a substantially hollow shaft having a proximal end and a distal end;
the driveline extending within the hollow shaft, the driveline having:
a proximal end connectable to a rotational power tool for applying torque through the driveline; and
said head part extending distally from the distal end of the shaft, the head part having an axis of rotation for rotation of the surgical rotational tool on rotation of the driveline, the connection features of the head part comprising:
a housing;
a pair of jaw members, each jaw member including a pair of jaws for receiving the connection member of the surgical rotational tool, wherein each jaw member is pivotally mounted on the housing for rotation about an axis substantially perpendicular to the axis of rotation of the head part between:
a first position for receipt of the connection member within the jaws of each jaw member; and a second position for retaining the connection member within the jaws of each jaw member to prevent removal of the surgical rotation tool from the surgical rotational tool driver; and a locking mechanism comprising:

a pair of ramps for engaging with a respective catch of each jaw member to lock the jaw members in the second position, and a release member slideably moveable within the housing to release the ramps of the locking mechanism from the respective catches of the jaw members to allow the jaw members to return to the first position for removal of the surgical rotational tool from the surgical rotational tool driver;

riding the catch of each jaw member along a respective ramped surface extending laterally from the release member as the jaw members pivot from the first position to the second position and engaging the catches of the jaw members with retaining surfaces located at an end of the respective ramped surfaces when they reach the end of the ramped surfaces, to lock the jaw members in the second position;

operating the release mechanism by sliding the release member within the housing; and removing the surgical rotational tool from the surgical rotational tool driver.

17. The method of claim 16, further comprising sliding the release member within the housing to disengage the catch of each jaw member from the retaining surfaces of the respective ramped surfaces on the release member.

18. The method of claim 17, comprising sliding the release member along a direction substantially parallel to the axis of rotation of the head part.

* * * * *